US012728120B2

(12) United States Patent
Lee et al.

(10) Patent No.: US 12,728,120 B2
(45) Date of Patent: Sep. 8, 2026

(54) PREVENTION OR TREATMENT OF BRAIN DISEASE AND ADVERSE EFFECTS OF CHOLINESTERASE INHIBITORS

(71) Applicant: DR. NOAH BIOTECH INC., Suwon-si (KR)

(72) Inventors: Ji Hyun Lee, Suwon-si (KR); Eun Jung Kim, Suwon-si (KR)

(73) Assignee: Dr. Noah Biotech Inc., Suwon-si (KR)

(*) Notice: Subject to any disclaimer, the term of this patent is extended or adjusted under 35 U.S.C. 154(b) by 454 days.

(21) Appl. No.: 18/359,955

(22) Filed: Jul. 27, 2023

(65) Prior Publication Data

US 2024/0066017 A1 Feb. 29, 2024

Related U.S. Application Data

(63) Continuation-in-part of application No. PCT/KR2021/015350, filed on Oct. 28, 2021.

(30) Foreign Application Priority Data

Jan. 28, 2021 (KR) ........................ 10-2021-0012659
Dec. 16, 2022 (KR) ........................ 10-2022-0177363

(51) Int. Cl.

| | |
|---|---|
| ***A61K 31/4453*** | (2006.01) |
| ***A61K 31/197*** | (2006.01) |
| ***A61K 31/445*** | (2006.01) |
| ***A61P 25/28*** | (2006.01) |
| ***A61P 29/00*** | (2006.01) |
| *A61K 31/198* | (2006.01) |

(52) U.S. Cl.

CPC ............ *A61K 31/445* (2013.01); *A61P 25/28* (2018.01); *A61P 29/00* (2018.01); *A61K 31/198* (2013.01)

(58) Field of Classification Search

CPC ... A61K 31/4453; A61K 31/197; A61P 25/00; A61P 25/28

USPC .................................................. 514/319, 562

See application file for complete search history.

(56) References Cited

U.S. PATENT DOCUMENTS

| | | | | |
|---|---|---|---|---|
| 6,369,106 B1 | | 4/2002 | Atlas | |
| 8,597,640 B2 * | | 12/2013 | Shea | .................... A61K 31/525 514/579 |
| 2002/0128319 A1 | | 9/2002 | Koo | |
| 2004/0132666 A1 | | 7/2004 | Neuwelt | |

FOREIGN PATENT DOCUMENTS

| | | | | |
|---|---|---|---|---|
| EP | 1514542 A1 | | 3/2005 | |
| JP | 4373087 B2 | | 11/2009 | |
| KR | 1020190129000 | | 11/2019 | |
| WO | WO 2004-034963 A2 | * | 4/2004 | ......... A61K 31/4453 |
| WO | WO 2017-004436 A2 | * | 1/2017 | ........... A61K 31/202 |

OTHER PUBLICATIONS

Schmitt, B. et al.: Combination therapy in Alzheimer's disease. CNS Drugs, vol. 18, pp. 827-844, 2004.*

Yang et al. Combining antioxidant astaxantin and cholinesterase inhibitor huperzine A boosts neuroprotection. Molecular Medicine Reports. 2020, vol. 21, pp. 1043-1050.

Bliss. The toxicity of poisons applied jointly. Annals of Applied Biology. 1939, vol. 26, issue 3 ,pp. 585-615.

Tanaka et al. Post-ischemic administration of the acetylcholinesterase inhibitor ENA-713 prevents delayed neuronal death in the gerbil hippocampus. Neurochemical Research. 1995, vol. 20, No. 6, pp. 663-667.

Mizuno et al. CREB phosphorylation as a molecular marker of memory processing in the hippocampus for spatial learning. Behavioural Brain Research. 133 (2002), pp. 135-141.

Fujiki et al. Neuroprotective effect of donepezil, a nicotinic acetylcholine-receptor activator, on cerebral infarction in rats. Brain Research. 1043 (2005), pp. 236-241.

Ehrlich et al. PSD-95 is required for activity-driven synapse stabilization. Proceedings of the National Academy of Sciences. Mar. 6, 2007, vol. 104, No. 10, pp. 4176-4181.

Cuzzocrea et al. Beneficial effects of n-acetylcysteine on ischaemic brain injury. British Journal of Pharmacology. 2000, 130, pp. 1219-1226.

Cornelli. Treatment of alzheimer's disease with a cholinesterase inhibitor combined with antioxidants. Neurodegenerative Diseases. 2010, vol. 7, pp. 193-202.

Nagura et al. Impaired synaptic clustering of postsynaptic density proteins and altered signal transmission in hippocampal neurons, and disrupted learning behavior in PDZ1 and PDZ2 ligand bindingdeficient PSD-95 knockin mice. Molecular Brain. 2012, 5:43.

Kida et al. Functional roles of CREB as a positive regulator in the formation and enhancement of memory. Brain Research Bulletin. 2014, vol. 105, pp. 17-24.

* cited by examiner

*Primary Examiner* — Charanjit Aulakh

(74) *Attorney, Agent, or Firm* — Choi Capital Law PLLC; Kevin J Fournier

(57) ABSTRACT

Compositions and methods are described for alleviating, preventing, or treating adverse effects of cholinesterase inhibitors by administering an effective amount of an antioxidant to a subject in need thereof. Composition and methods are described for preventing or treating a brain disease by administering a cholinesterase inhibitor and an antioxidant to a subject in need thereof.

4 Claims, 16 Drawing Sheets

P-AKT/AKT Expression

***
***
***
***
1500
1000
500
0
Relative P-AKT Expression (P-AKT/AKT)
Normal
Vehicle
Donepezil (1 mpk)
N-Acetylcysteine (120 mpk)
NDC-002 (1+120 mpk)

P-ERK/ERK Expression

PREVENTION OR TREATMENT OF BRAIN DISEASE AND ADVERSE EFFECTS OF CHOLINESTERASE INHIBITORS

TECHNICAL FIELD

The present disclosure relates to a method for alleviating, preventing or treating adverse effects of cholinesterase inhibitors, comprising administering an effective amount of an antioxidant to a subject in need thereof. The present disclosure also relates to a method for preventing or treating a brain disease, comprising administering a cholinesterase inhibitor and an antioxidant to a subject in need thereof. The present disclosure also provides a composition for preventing or treating a brain disease, comprising a cholinesterase inhibitor and an antioxidant as active ingredients.

BACKGROUND OF THE INVENTION

According to data released by Statistics Korea in 2010, the number of elderly people aged 65 and over accounted for 11.4% of the total population in 2011, and is expected to reach 37.4% by 2050, making Korea an ultra-aging society. As the aging problem has become a social issue in recent years, the public's interest in the characteristics of the elderly population and the welfare of the elderly, including housing, health, culture, and leisure, is increasing. The growth of the aging population makes chronic degenerative diseases a bigger problem than acute infectious diseases, which have been the leading cause of death for the past 50 years. Among chronic degenerative disorders, cerebrovascular disease is a very important one, ranking second in terms of single-cause mortality.

Cerebrovascular diseases include hemorrhagic brain disease caused by a cerebral hemorrhage, and ischemic brain disease caused by a blockage in blood vessels of the brain. In cerebral ischemia, the supply of oxygen and glucose to the brain is cut off, causing neurons to experience reduced ATP and edema, leading to extensive brain damage. Neuronal death occurs a significant number of times after cerebral ischemia, which is called delayed neuronal death.

Also, Alzheimer's disease is one of the common brain diseases these days, which occurs mainly in the elderly population over the age of 60. Research on the pathogenesis of these diseases, particularly, in view of the aging of the Korean population, which is progressing at a very fast pace, and the serious psychological distress and economic burden it can cause not only to the patients themselves, but also to their families, society, and the country is essential.

Dementia is a group of cognitive disorders characterized by memory loss, decline in intelligence, personality changes, and behavioural abnormalities. It is a degenerative neurological disease that is caused by irreversible dysfunction in the neural circuit network due to slow neuronal death that causes degenerative disorders of the central nervous system, and eventually leads to permanent loss of human functions. The cause of dementia has not yet been clearly identified, and since it has various etiological and pathophysiological factors, there is no treatment that can fundamentally treat dementia.

Acetylcholinesterase (AChE) inhibitors such as Donepezil (trade name: Aricept), tacrine (trade name: Cognex), rivastigmine (trade name: Exelon), Galantamine (trade name: Reminyl), etc. are known as the potential drugs for the treatment of Brain conditions such as Alzheimer's disease, Dementia, Brain stroke, etc. However, systemic administration of AChE inhibitors, including donepezil, affects not only the target tissues but also other tissues, resulting in various adverse effects such as diarrhea, nausea, dizziness, salivation, anxiety, tremor, lethargy, muscle spasms, decreased body temperature, extrapyramidal symptoms, miosis and the likes, which limits their long-term use.

Therefore, there is a need to develop a method of alleviation, prevention or treatment of the adverse effect of AChE inhibitors, so that they can be taken safely for a recommended/desired period of time to promote neuronal differentiation and protection.

SUMMARY

The present invention relates to compositions and methods for alleviating, preventing or treating one or more adverse effects of a cholinesterase inhibitor, the method comprising administering an effective amount of an antioxidant to a subject in need thereof. In some embodiments, the method comprises administration of an antioxidant before, simultaneously with, or after administration of the cholinesterase inhibitor.

The present invention also relates to compositions and methods for preventing or treating a brain disease, comprising administering a cholinesterase inhibitor and an antioxidant to a subject in need thereof. In some embodiments, the method comprises administration of an antioxidant before, simultaneously with, or after administration of the cholinesterase inhibitor.

The present invention also relates to compositions and methods for treating a neurodegenerative disease, comprising administering a cholinesterase inhibitor and an antioxidant to a subject in need thereof. In some embodiments, the method comprises administration of an antioxidant before, simultaneously with, or after administration of the cholinesterase inhibitor.

The present disclosure also relates to compositions and methods for promoting neuronal differentiation, comprising administering a cholinesterase inhibitor and an antioxidant to a subject in need thereof. In some embodiments, the method comprises administration of an antioxidant before, simultaneously with, or after administration of the cholinesterase inhibitor.

BRIEF DESCRIPTION OF DRAWINGS

The foregoing summary, as well as the following detailed description of the embodiments, will be better understood when read in conjunction with the attached drawings. For the purpose of illustration, there are shown in the drawings, some embodiments, which may be preferable. It should be understood that the embodiments depicted are not limited to the precise details shown, and are not drawn to scale.

DETAILED DESCRIPTION OF THE INVENTION

Figure 1:
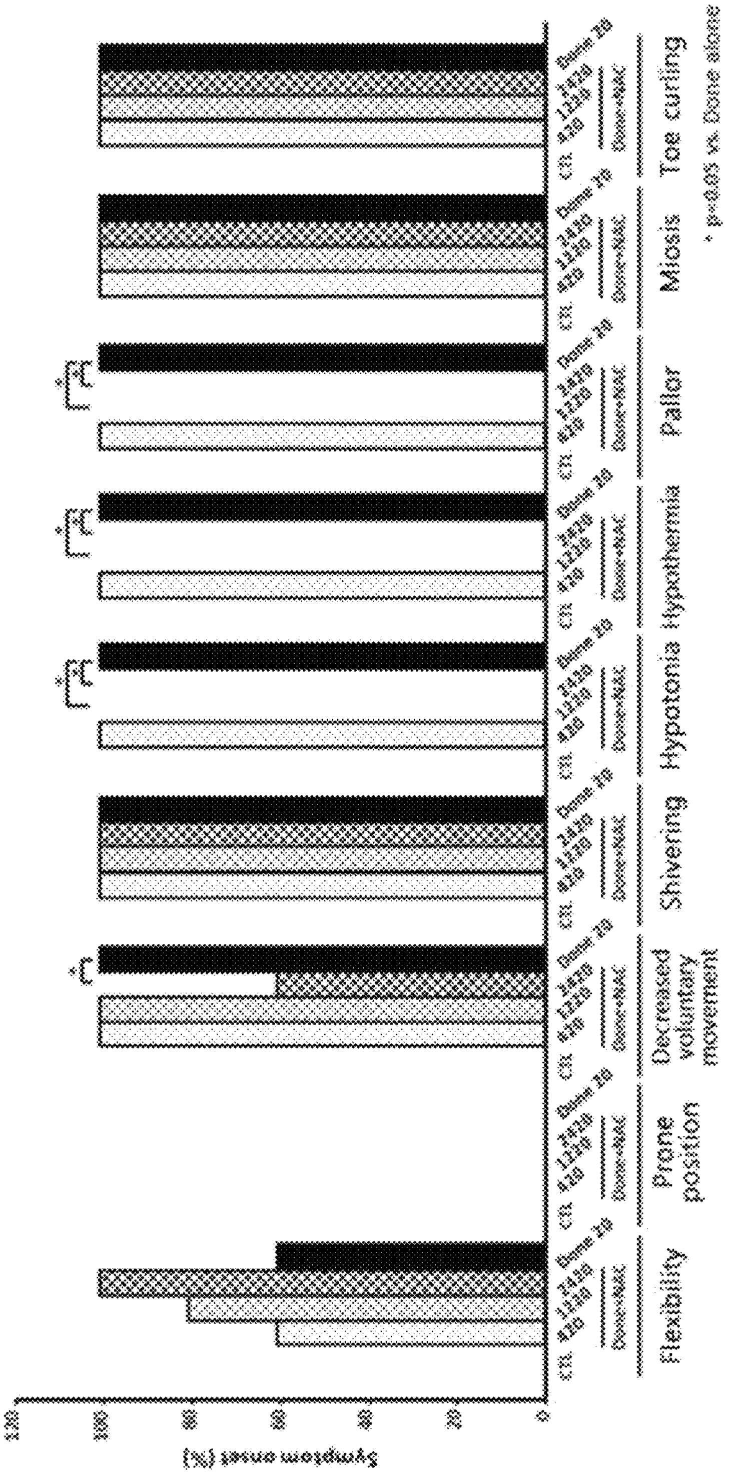
FIG. 1 illustrates the incidence of adverse effects caused by donepezil in female rats to which either donepezil alone or a combination of donepezil and N-acetylcysteine was administrated.

In the following description, reference is made to the accompanying drawings, which form a part hereof. In the drawings, similar symbols typically identify similar components, unless context dictates otherwise. The illustrative embodiments described in the detailed description, drawings and claims are not meant to be limiting. Other embodiments may be utilized, and other changes may be made, without departing from the spirit or scope of the subject matter presented herein.

Unless otherwise noted, all measurements are in standard metric units. Unless otherwise noted, all instances of the words "a," "an," or "the" can refer to one or more than one of the words that they modify.

As used herein, donepezil is referred to as "Done", "DONE" or "donepezil HCl" synonymously and interchangeably.

As used herein, N-acetylcysteine is referred to as "NAC" synonymously and interchangeably.

As used herein, the combination of donepezil and N-acetylcysteine is referred to as "NDC", "NDC-002", "donepezil+NAC", "Done+NAC" or "donepezil HCl+NAC" synonymously and interchangeably.

As used herein, the term "subject" refers to an animal, preferably a mammal, and most preferably a human. The term "mammal" used herein refers to warm-blooded vertebrate animals of the class "mammalia", including humans, characterized by a covering of hair on the skin and, in the female, milk-producing mammary glands for nourishing the young ones. The term mammal includes animals such as cat, dog, rabbit, bear, fox, wolf, monkey, deer, mouse, pig and human.

As used herein, the term "adverse effects" refers to all abnormal symptoms other than the therapeutic effect that may occur by administration of a cholinesterase inhibitor in a therapeutically effective amount or more, and the type is not particularly limited. By way of example, various adverse effects reported to be causally related to administration of donepezil, a cholinesterase inhibitor, include syncope, bradycardia, cardiac block, QT interval prolongation, myocardial infarction, heart failure, asthenia, hypothermia, urinary incontinence, rash, miosis, anorexia, diarrhoea, nausea, abdominal pain, nausea, peptic ulcer, salivation (drooling, flaccidity), perforated duodenal perforation, gastrointestinal bleeding, hepatitis, liver dysfunction, jaundice, insomnia, hallucinations, drowsiness, dizziness, tremor, stupor, cerebral seizures (epilepsy, convulsions, etc.), cerebral haemorrhage, cerebrovascular disorders, extrapyramidal disorders (motor dysfunction, ataxia, decreased voluntary movement, dystonia, tremor, gait disorder, abnormal posture, speech disorder), ataxia, extreme muscle stiffness, dysphagia, tachycardia, bradycardia, blood pressure fluctuations (hypertension, hypotension), sweating (tremors), and pallor, fever, rhabdomyolysis (muscle pain, weakness, increased CK (CPK) in blood and urine), dyspnoea, acute pancreatitis, acute renal failure and sudden death of unknown cause.

As used herein, the term "therapeutically effective amount" refers to an amount of a cholinesterase inhibitor indicated for its therapeutic use. In some embodiments, the therapeutically effective amount of a cholinesterase inhibitor may be the same as clinically approved amount of a cholinesterase inhibitor for a particular indication (for example, symptomatic treatment of dementia in Alzheimer's disease).

As used herein, the term "cholinesterase inhibitor" refers to a compound or drug that inhibits the enzymatic degradation of the neurotransmitter acetylcholine and increases the duration and level of acetylcholine action in the synaptic cleft. Two enzymes are primarily responsible for the breakdown of acetylcholine namely acetylcholinesterase and butyrylcholinesterase. The "cholinesterase inhibitor" comprises substances that inhibit or otherwise reduce the action of one or both of these enzymes.

As used herein, the term "pharmaceutically effective" refers to cholinesterase inhibitors that are therapeutically useful in humans. The term excludes cholinesterase inhibitors used as pesticides, such as aldicarb (2-methyl-2-(methylthio)propionaldehyde O-methylcarbamoyloxime), carbofuran (2,3-dihydro-2,2-dimethyl-7-benzofuranyl methylcarbamate), and carbaryl (1-naphthyl methylcarbamate), and cholinesterase inhibitors that are lethal enough to humans to be used as chemical weapons, such as sarin (2-(fluoro-methylphosphoryl)oxypropane), VX (S-[2-(diisopropylamino)ethyl]-O-ethyl methylphosphonothioate), and soman (3-(fluoro-methyl-phosphoryl)oxy-2,2-dimethyl-butane).

As used herein, the term "antioxidant" refers to a substance that helps protect the human body from oxidative stress by removing active oxygen species generated in the body.

The term "active ingredient(s)" or "drug(s)" are used synonymously and interchangeably throughout the description, and they represent the one or more cholinesterase inhibitor(s) and/or antioxidant(s).

As used herein, the term "Bliss Independence" refers to a predicted combined response C for two single drug(s) with effects A and B, wherein C is =A+B−A*B and where each effect is expressed as a fractional inhibition (or promotion) value from 0 to 1 (see Bliss (1939) Annals of Applied Biology).

As used herein, the term "Bliss Value" is the difference between the actual experimental response and the predicted response calculated using Bliss Independence model.

$$\text{Bliss Value} = C_{AB} - C_{Bliss}$$

$$C_{Bliss} = C_A + C_B - C_A * C_B$$

Wherein, $C_{Bliss}$ represents the predicted effect of a drug combination calculated using Bliss Independence model; $C_A$ and $C_B$ represent the actual effect, measured from experiment, of single drug A and B, respectively, expressed as a fractional value in the range of 0 and 1; and $C_{AB}$ represents the actual effect of the drug combination measured from experiment. A Bliss Value of zero (0) means that the combined effect of two drugs is additive. A Bliss Value greater than zero means that the two drugs are synergistic. A Bliss Value less than zero means two drugs are antagonistic.

As used herein, the term "additive" means that the effect obtained by combining two different drugs is the sum of the effects obtained by each individual drug. A Bliss Value of zero (0) is considered an additive effect.

The terms "synergy" or "synergism" or "synergistic" are used synonymously and interchangeably throughout the description and they mean that the effect obtained by combining two different drugs is greater than the sum of each of the individual drug. A Bliss Value of greater than zero is considered synergism.

The term "Bliss Synergy" means that the actual effect of a drug combination measured from experiment ($C_{AB}$) exceeds the predicted effect of drug combination calculated using Bliss Independence model ($C_{Bliss}$). Although the present disclosure uses Bliss Independence model, other methods, such as Loewe's model, may also be utilized for determination of synergy.

As used herein, the term "ischemic" or "ischemia" refers to cerebrovascular diseases, and any pathological abnormality in the blood vessels supplying blood to the brain due to thrombosis, embolism, cerebrovascular thickening, cerebrovascular occlusion, and the likes, without any limitation thereof. Non-limiting examples of the ischemic diseases include stroke, cerebral hemorrhage, cerebral infarction, head trauma, cerebral circulatory metabolic disorder, vascular dementia, and cerebral functional coma.

As used herein, the term "prevention" refers to any action that reduces the frequency or severity of pathological phenomena. It can be complete or partial. It includes any phenomenon in which the symptoms are reduced in a subject as compared a subject where the agent or the composition is/are not used.

As used herein, the term "treatment" refers to any act that intervenes clinically to change the natural process of a target or cell to be treated. It can be performed while the clinical pathology is progressing.

As used herein, the term "therapeutic effect" refers to preventing occurrence or recurrence of a disease, alleviating the symptoms thereof, reducing any direct or indirect pathological consequences of the disease, reducing the rate of disease progression, alleviating or temporarily relieving a disease condition, or improving prognosis.

As used herein, the phrase "in need thereof" refers to a judgment made by a caregiver such as a physician or veterinarian that a patient requires (or will benefit in one or more ways) from treatment. Such judgment may be made based on a variety of factors that are in the realm of a caregiver's expertise, and may include the knowledge that the patient is ill as the result of a disease state that is treatable by one or more drug(s) or pharmaceutical compositions or formulations.

As used herein, the term "simultaneously" refers to administering the two active ingredients together via the same route of administration, or administering them separately via the same or different routes of administration at substantially the same time (e.g., within a time interval of 15 minutes or less between administrations).

As used herein, the term "pharmaceutically acceptable carrier" means the material incorporated into a pharmaceutical composition administered to a subject without causing any undesirable biological effects or interacting in a deleterious manner with any of the other components of the composition in which it is contained.

As used herein, the term "pharmaceutically effective amount" refers to an amount of a combination of cholinesterase inhibitor(s) and antioxidant(s) that produces a reaction that is greater than or equal to that of a negative control, preferably an amount sufficient to increase lifespan, improve mobility, inhibit neuroinflammation, inhibit neuronal cell death, promote neuroprotection or promote neuronal cell differentiation by co-administration of the two active ingredients in treating or preventing brain disease.

Cholinesterase inhibitor(s) are known as the potential drugs for the treatment of brain conditions such as Alzheimer disease, Dementia, Brain stroke, etc. However, administration of cholinesterase inhibitors results in various adverse effects such as diarrhea, nausea, dizziness, salivation, anxiety, tremor, lethargy, muscle spasms, decreased body temperature, extrapyramidal symptoms, miosis and the likes, which limits their long-term use.

In one aspect, the present invention is directed to preventing, alleviating, or treating symptoms associated with the use of cholinesterase inhibitor(s) for its therapeutic effect in neurodegenerative disorders. The present disclosure solves the problem(s) of one or more adverse effects coupled with ingestion or administration of one or more cholinesterase inhibitors by providing a method of alleviation, prevention or treatment of one or more adverse effects caused by a cholinesterase inhibitor, the method comprising administering an effective amount of an antioxidant to a subject in need thereof. Administration of the antioxidant can afford prevention, alleviation, or treatment of one or more adverse effects caused by administration of a cholinesterase inhibitor. The antioxidant, when administered before, simultaneously with, or after administration of the cholinesterase inhibitor exhibits a synergistic effect, while treating, preventing, or alleviating, one or more adverse effects associated with administration of the cholinesterase inhibitor alone.

An aspect of the present disclosure relates to a method for alleviating, preventing, or treating one or more adverse effects of a cholinesterase inhibitor, the method comprising administering an effective amount of an antioxidant to a subject in need thereof. In some embodiments, the present invention is directed to a method for alleviating, preventing, or treating one or more adverse effects caused by administration of a therapeutically effective amount of a cholinesterase inhibitor.

In some embodiments, the cholinesterase inhibitor can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

In some embodiments, the antioxidant can be selected from any or a combination of: N-acetylcysteine (NAC), ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine (NAC), alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the antioxidant is administered orally or parenterally. Parenteral administration may include, but is not limited to, intravenous, intramuscular, intra-arterial, intramedullary, intrathecal, intracardiac, transdermal, subcutaneous, intracerebroventricular (subventricular zone), intracerebral, intraperitoneal, intranasal, enteral, topical, sublingual, or rectal administration.

In some embodiments, an effective amount of the antioxidant is administered for alleviating, preventing, or treating the one or more adverse effects caused by administration of a cholinesterase inhibitor in a subject. In some embodiment, an effective amount of the antioxidant is administered for alleviating, preventing or treating the one or more adverse effects caused by administration of a therapeutically effective amount of cholinesterase inhibitor in a subject. In a preferred embodiment, the effective amount of the antioxidant is about 30 to about 240 times the amount of the cholinesterase inhibitor taken by (or administered to) the subject, about 30 to about 230 times the amount of the cholinesterase inhibitor taken by (or administered to) the subject, about 30 to about 220 times the amount of the cholinesterase inhibitor taken by (or administered to) the subject, about 30 to about 210 times the amount of the cholinesterase inhibitor taken by (or administered to) the subject, about 30 to about 200 times the amount of the cholinesterase inhibitor taken by (or administered to) the subject, about 30 to about 190 times the amount of the cholinesterase inhibitor taken by (or administered to) the subject, about 30 to about 180 times the amount of the cholinesterase inhibitor taken by (or administered to) the subject, about 30 to about 170 times the amount of the cholinesterase inhibitor taken by (or administered to) the subject, about 30 to about 160 times the amount of the cholinesterase inhibitor taken by (or administered to) the subject, about 30 to about 150 times the amount of the cholinesterase inhibitor taken by (or administered to) the subject, about 30 to about 140 times the amount of the cholinesterase inhibitor taken by (or administered to) the subject, about 30 to about 130 times the amount of the cholinesterase inhibitor taken by (or administered to) the subject, about 30 to about 120 times the amount of the cholinesterase inhibitor taken by (or administered to) the subject, about 30 to about 110 times the amount of the cholinesterase inhibitor taken by (or administered to) the subject, about 30 to about 100 times the amount of the cholinesterase inhibitor taken by (or administered to) the subject, about 30 to about 90 times the amount of the cholinesterase inhibitor taken by (or administered to) the subject, about 30 to about 80 times the amount of the cholinesterase inhibitor taken by (or administered to) the subject, about 30 to about 70 times the amount of the cholinesterase inhibitor taken by (or administered to) the subject, about 30 to about 60 times the amount of the cholinesterase inhibitor taken by (or administered to) the subject, about 30 to about 50 times the amount of the cholinesterase inhibitor taken by (or administered to) the subject, about 30 to about 40 times the amount of the cholinesterase inhibitor taken by (or administered to) the subject, about 40 to about 230 times the amount of the cholinesterase inhibitor taken by (or administered to) the subject, about 40 to about 220 times the amount of the cholinesterase inhibitor taken by (or administered to) the subject, about 40 to about 210 times the amount of the cholinesterase inhibitor taken by (or administered to) the subject, about 40 to about 200 times the amount of the cholinesterase inhibitor taken by (or administered to) the subject, about 40 to about 190 times the amount of the cholinesterase inhibitor taken by (or administered to) the subject, about 40 to about 180 times the amount of the cholinesterase inhibitor taken by (or administered to) the subject, about 40 to about 170 times the amount of the cholinesterase inhibitor taken by (or administered to) the subject, about 40 to about 160 times the amount of the cholinesterase inhibitor taken by (or administered to) the subject, about 40 to about 150 times the amount of the cholinesterase inhibitor taken by (or administered to) the subject, about 40 to about 140 times the amount of the cholinesterase inhibitor taken by (or administered to) the subject, about 40 to about 130 times the amount of the cholinesterase inhibitor taken by (or administered to) the subject, about 40 to about 120 times the amount of the cholinesterase inhibitor taken by (or administered to) the subject, about 40 to about 110 times the amount of the cholinesterase inhibitor taken by (or administered to) the subject, about 40 to about 100 times the amount of the cholinesterase inhibitor taken by (or administered to) the subject, about 40 to about 90 times the amount of the cholinesterase inhibitor taken by (or administered to) the subject, about 40 to about 80 times the amount of the cholinesterase inhibitor taken by (or administered to) the subject, about 40 to about 70 times the amount of the cholinesterase inhibitor taken by (or administered to) the subject, about 40 to about 60 times the amount of the cholinesterase inhibitor taken by (or administered to) the subject, about 40 to about 50 times the amount of the cholinesterase inhibitor taken by (or administered to) the subject, about 50 to about 230 times the amount of the cholinesterase inhibitor taken by (or administered to) the subject, about 50 to about 220 times the amount of the cholinesterase inhibitor taken by (or administered to) the subject, about 50 to about 210 times the amount of the cholinesterase inhibitor taken by (or administered to) the subject, about 50 to about 200 times the amount of the cholinesterase inhibitor taken by (or administered to) the subject, about 50 to about 190 times the amount of the cholinesterase inhibitor taken by (or administered to) the subject, about 50 to about 180 times the amount of the cholinesterase inhibitor taken by (or administered to) the subject, about 50 to about 170 times the amount of the cholinesterase inhibitor taken by (or administered to) the subject, about 50 to about 160 times the amount of the cholinesterase inhibitor taken by (or administered to) the subject, about 50 to about 150 times the amount of the cholinesterase inhibitor taken by (or administered to) the subject, about 50 to about 140 times the amount of the cholinesterase inhibitor taken by (or administered to) the subject, about 50 to about 130 times the amount of the cholinesterase inhibitor taken by (or administered to) the subject, about 50 to about 120 times the amount of the cholinesterase inhibitor taken by (or administered to) the subject, about 50 to about 110 times the amount of the cholinesterase inhibitor taken by (or administered to) the subject, about 50 to about 100 times the amount of the cholinesterase inhibitor taken by (or administered to) the subject, about 50 to about 90 times the amount of the cholinesterase inhibitor taken by (or administered to) the subject, about 50 to about 80 times the amount of the cholinesterase inhibitor taken by (or administered to) the subject, about 50 to about 70 times the amount of the cholinesterase inhibitor taken by (or administered to) the subject, about 50 to about 60 times the amount of the cholinesterase inhibitor taken by (or administered to) the subject, about 60 to about 230 times the amount of the cholinesterase inhibitor taken by (or administered to) the subject, about 60 to about 220 times the amount of the cholinesterase inhibitor taken by (or administered to) the subject, about 60 to about 210 times the amount of the cholinesterase inhibitor taken by (or administered to) the subject, about 60 to about 200 times the amount of the cholinesterase inhibitor taken by (or administered to) the subject, about 60 to about 190 times the amount of the cholinesterase inhibitor taken by (or administered to) the subject, about 60 to about 180 times the amount of the cholinesterase inhibitor taken by (or administered to) the subject, about 60 to about 170 times the amount of the cholinesterase inhibitor taken by (or administered to) the subject, about 60 to about 160 times the amount of the cholinesterase inhibitor taken by (or administered to) the subject, about 60 to about 150 times the amount of the cholinesterase inhibitor taken by (or administered to) the subject, about 60 to about 140 times the amount of the cholinesterase inhibitor taken by (or administered to) the subject, about 60 to about 130 times the amount of the cholinesterase inhibitor taken by (or administered to) the subject, about 60 to about 120 times the amount of the cholinesterase inhibitor taken by (or administered to) the subject, about 60 to about 110 times the amount of the cholinesterase inhibitor taken by (or administered to) the subject, about 60 to about 100 times the amount of the cholinesterase inhibitor taken by (or administered to) the subject, about 60 to about 90 times the amount of the cholinesterase inhibitor taken by (or administered to) the subject, about 60 to about 80 times the amount of the cholinesterase inhibitor taken by (or administered to) the subject, or about 60 to about 70 times the amount of the cholinesterase inhibitor taken by (or administered to) the subject.

In some embodiments, a cholinesterase inhibitor is used for its therapeutic effect in neurodegenerative disorders such as Alzheimer's disease, dementia, Parkinson's disease, cognitive dysfunction, progressive supranuclear palsy, multiple system atrophy, olive-pontine-cerebellar atrophy (OPCA), Shy-Drager syndrome, striatal-substantia nigra degeneration, Huntington's disease, amyotrophic lateral sclerosis (ALS), essential tremor, cortico-basal ganglia degeneration, diffuse Lewy body disease, Parkinson-ALS-dementia complex, Niemann-Pick disease and Pick disease.

In some embodiments, the one or more adverse effects of cholinesterase inhibitor(s) include, but not limited to, any or a combination of: extrapyramidal symptoms, asthenia, hypothermia, tremor, convulsions, pallor, sickness, bradycardia, hypotension, anorexia, diarrhea, nausea, insomnia, hallucinations, drowsiness, dizziness, incontinence, rash, miosis and drooling. In some embodiments, the extrapyramidal symptom is selected from the group comprising: motor dysfunction, ataxia, decreased spontaneous movement, dystonia, tremor, gait disorder, abnormal posture, and speech disorder.

In some embodiments, the one or more adverse effects of cholinesterase inhibitor is caused by oral or transdermal administration of one or more cholinesterase inhibitors. In some embodiments, the one or more adverse effects of cholinesterase inhibitor is caused by oral or transdermal administration of a therapeutically effective amount of one or more cholinesterase inhibitors. In some embodiments, the one or more adverse effects of cholinesterase inhibitor is caused by oral or transdermal administration, by a single or repeated administration, of a cholinesterase inhibitor, for instance, by administration of 0.05 mg/kg/day to 0.125 mg/kg/day or more of one or more cholinesterase inhibitors. In some embodiments, the one or more adverse effects is caused by a daily oral or transdermal administration, by single or repeated, administration of 5 mg, 10 mg or more of one or more cholinesterase inhibitors.

In some embodiments, the one or more adverse effects is caused by oral or transdermal administration, by a single or repeated administration, of 0.05 mg/kg/day to 0.125 mg/kg/day or more of donepezil. In some embodiments, the one or more adverse effects is caused by daily oral or transdermal administration, by a single or repeated administration of 5 mg, 10 mg, 23 mg or more of donepezil.

In some embodiments, the cholinesterase inhibitor is donepezil or a salt thereof. Donepezil is an acetylcholinesterase (AChE) inhibitor having a structure represented by Formula 1 below and is used for the treatment of brain diseases including Ischemia, Alzheimer's disease, and dementia. Donepezil, currently used commercially, is in the form of a tablet (pill) and is being prescribed to patients with Alzheimer's disease in the form of an oral drug. In Alzheimer's disease, in which cholinergic nervous system disorders in the brain have been reported, donepezil activates cholinergic neurons in the brain by increasing acetylcholine in the brain.

[Formula 1]

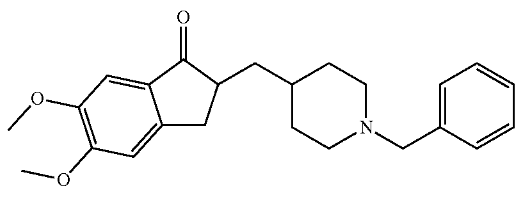

As a pharmaceutically acceptable salt of donepezil, an acid addition salt with a pharmaceutically acceptable free acid is useful. Acid addition salts are obtained from inorganic acids such as hydrochloric acid, nitric acid, phosphoric acid, sulfuric acid, hydrobromic acid, hydroiodic acid, nitrous acid or phosphorous acid and non-toxic organic acids such as aliphatic mono- and dicarboxylates, phenyl-substituted alkanoates, hydroxy alkanoates and alkanedioates, aromatic acids, aliphatic and aromatic sulfonic acids. These pharmaceutically non-toxic salts include, but not limited to, sulfate, pyrosulfate, bisulphate, sulphite, bisulfite, nitrate, phosphate, monohydrogen phosphate, dihydrogen phosphate, metaphosphate, pyrophosphate chloride, bromide, ioda Id, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, toxybenzoate, phthalate, terephthalate, benzenesulfonate, toluenesulfonate, chlorobenzenesulfonate, xylenesulfonate, phenylacetate, phenylpropionate, phenyl butyrate, citrate, lactate, β-hydroxybutyrate, glycol Late, maleate, tartrate, methanesulfonate, propanesulfonate, naphthalene-1-sulfonate, naphthalene-2-sulfonate or mandelate. In some embodiments, donepezil salt is hydrochloride salt of donepezil.

In some embodiments, the adverse effects are caused by the administration of donepezil. In some embodiments, the adverse effects are caused by the administration of a therapeutically effective amount of donepezil. In some embodiments, the adverse effects caused by donepezil includes: 1) Syncope, bradycardia, cardiac block, QT interval prolongation, myocardial infarction, heart failure, asthenia, hypothermia, urinary incontinence, rash, miosis; 2) Anorexia, diarrhea, nausea, abdominal pain, nausea, peptic ulcer, salivation (drooling, flaccidity), perforated duodenal perforation, gastrointestinal bleeding; 3) Hepatitis, liver dysfunction, jaundice; 4) Insomnia, hallucinations, drowsiness, dizziness, tremor, stupor, cerebral seizures (epilepsy, convulsions, etc.), cerebral hemorrhage, cerebrovascular disorders; 5) Extrapyramidal disorders: motor dysfunction, ataxia, decreased voluntary movement, dystonia, tremor, gait disorder, abnormal posture, speech disorder; 6) Symptoms such as ataxia, extreme muscle stiffness, dysphagia, tachycardia, bradycardia, blood pressure fluctuations (hypertension, hypotension), sweating (tremors), and pallor may occur, and these symptoms are usually accompanied by fever; 7) since rhabdomyolysis may occur, muscle pain, weakness, increased CK (CPK) in blood and urine; 8) Dyspnoea; 9) Acute pancreatitis; 10) Acute renal failure; and 11) Sudden death of unknown cause.

In some embodiments, the antioxidant is N-acetylcysteine or a salt thereof. The N-acetylcysteine is a drug for inhibiting or reducing oxidative stress, having a structure of Formula 2 represented herein-below.

[Formula 2]

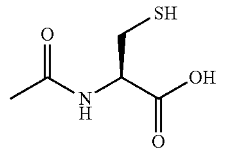

N-acetylcysteine was synthesized about 50 years ago and is mainly used as an expectorant or for the treatment of acetaminophen poisoning, which is an analgesic. N-acetylcysteine is also known to exhibit antioxidant effects by directly reacting with peroxide, hydrogen peroxide, hydroxyl radical, etc., leading to reduction in oxidative stress and/or by indirectly increasing glutathione synthesis by providing cysteine (a raw material for glutathione biosynthesis). N-acetylcysteine has been used for decades in various clinical fields such as treatment of acute respiratory distress syndrome, treatment of acute pulmonary oxygen toxicity, and prevention of acute renal failure by contrast agents, and is known as a safe drug that does not cause any serious adverse effects.

In some embodiments, the antioxidant is administered before, simultaneously with, or after administration of the cholinesterase inhibitor.

In some embodiments, the composition is a pharmaceutical composition. In some embodiments, the composition is a food composition.

In some embodiments, the pharmaceutical composition further comprises a pharmaceutically acceptable carrier. The pharmaceutically acceptable carrier can be selected from any or a combination of: a diluent, a bulking agent, a solubilizer, a binder, a disintegrant, a chelating agent, a glidant, a flavoring agent, a coloring agent, a tonicity agent, a sweetening agent, a buffering agent, a preservative, a lubricant, an emulsifier, a suspending agent, and a solvent.

In some embodiments, the antioxidant is administered simultaneously with the cholinesterase inhibitor, for example, in form of a composition or a formulation. In some embodiments, the composition comprises: (a) a cholinesterase inhibitor selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof; and (b) an antioxidant selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof.

In some embodiments, the composition comprises the cholinesterase inhibitor selected from any or a combination of: donepezil, galantamine, rivastigmine or a salt thereof. In some embodiments, the composition comprises the antioxidant selected from any or a combination of: N-acetylcysteine, alpha-lipoic acid, danthron, vitamin E, or a salt thereof.

In some embodiments, the composition comprises donepezil hydrochloride and tiopronin. In some embodiments, the composition comprises donepezil hydrochloride and vitamin C. In some embodiments, the composition comprises donepezil hydrochloride and alpha-lipoic acid. In some embodiments, the composition comprises donepezil hydrochloride and scopoletin. In some embodiments, the composition comprises donepezil hydrochloride and forsythin. In some embodiments, the composition comprises donepezil hydrochloride and isoferulic acid. In some embodiments, the composition comprises donepezil hydrochloride and gamma-oryzanol. In some embodiments, the composition comprises donepezil hydrochloride and trans-anethole. In some embodiments, the composition comprises donepezil hydrochloride and thioctic acid. In some embodiments, the composition comprises donepezil hydrochloride and ligustrazine hydrochloride. In some embodiments, the composition comprises donepezil hydrochloride and cysteamine hydrochloride. In some embodiments, the composition comprises donepezil hydrochloride and salvianolic acid. In some embodiments, the composition comprises donepezil hydrochloride and vitamin E. In some embodiments, the composition comprises donepezil hydrochloride and vitamin E acetate. In some embodiments, the composition comprises donepezil hydrochloride and pinocembrin. In some embodiments, the composition comprises donepezil hydrochloride and verbascoside. In some embodiments, the composition comprises donepezil hydrochloride and secoisolariciresinol diglucoside. In some embodiments, the composition comprises donepezil hydrochloride and lappaconitine. In some embodiments, the composition comprises donepezil hydrochloride and ellagic acid. In some embodiments, the composition comprises donepezil hydrochloride and glutathione. In some embodiments, the composition comprises donepezil hydrochloride and danthron. In some embodiments, the composition comprises donepezil hydrochloride and gallic acid. In some embodiments, the composition comprises donepezil hydrochloride and L-selenomethionine. In some embodiments, the composition comprises donepezil hydrochloride and catechin. In some embodiments, the composition comprises donepezil hydrochloride and vitamin A. In some embodiments, the composition comprises donepezil hydrochloride and coenzyme Q10.

In some embodiments, the composition comprises galantamine and N-acetylcysteine. In some embodiments, the composition comprises rivastigmine and N-acetylcysteine. In some embodiments, the composition comprises N-acetylcysteine and pyridostigmine. In some embodiments, the composition comprises N-acetylcysteine and itopride hydrochloride. In some embodiments, the composition comprises N-acetylcysteine and acotiamide. In some embodiments, the composition comprises N-acetylcysteine and tacrine. In some embodiments, the composition comprises N-acetylcysteine and huperzine. In some embodiments, the composition comprises N-acetylcysteine and neostigmine. In some embodiments, the composition comprises N-acetylcysteine and 7-methoxytacrine. In some embodiments, the composition comprises N-acetylcysteine and albameline. In some embodiments, the composition comprises N-acetylcysteine and ambenonium. In some embodiments, the composition comprises N-acetylcysteine and arecoline. In some embodiments, the composition comprises N-acetylcysteine and cevimeline. In some embodiments, the composition comprises N-acetylcysteine and citicoline. In some embodiments, the composition comprises N-acetylcysteine and demacarium. In some embodiments, the composition comprises N-acetylcysteine and edrophonium. In some embodiments, the composition comprises N-acetylcysteine and eptastigmine. In some embodiments, the composition comprises N-acetylcysteine and fasciculin. In some embodiments, the composition comprises N-acetylcysteine and heptyl-physostigmine. In some embodiments, the composition comprises N-acetylcysteine and huperzine A. In some embodiments, the composition comprises N-acetylcysteine and icopezil. In some embodiments, the composition comprises N-acetylcysteine and ipidacrine. In some embodiments, the composition comprises N-acetylcysteine and linopiridine. In some embodiments, the composition comprises N-acetylcysteine and metrifonate. In some embodiments, the composition comprises N-acetylcysteine and milameline. In some embodiments, the composition comprises N-acetylcysteine and nomeostigmine. In some embodiments, the composition comprises N-acetylcysteine and norpyridostigmine. In some embodiments, the composition comprises N-acetylcysteine and tacrine. In some embodiments, the composition comprises N-acetylcysteine and physostigmine. In some embodiments, the composition comprises N-acetylcysteine and subcomeline. In some embodiments, the composition comprises N-acetylcysteine and suronacrine. In some embodiments, the composition comprises N-acetylcysteine and talsaclidine. In some embodiments, the composition comprises N-acetylcysteine and velnacrine. In some embodiments, the composition comprises N-acetylcysteine and xanomeline. In some embodiments, the composition comprises N-acetylcysteine and ziprasidone. In some embodiments, the composition comprises N-acetylcysteine and zifrosilone. In some embodiments, the composition comprises N-acetylcysteine and itopride.

In some embodiments, the composition comprises donepezil or a salt thereof, and N-acetylcysteine or a salt thereof. In some embodiments, the composition comprises donepezil and N-acetylcysteine. In some embodiments, the composition comprises donepezil hydrochloride and N-acetylcysteine.

In some embodiments, the composition is a pharmaceutical composition. In some embodiments, the composition is a food composition.

In some embodiments, the pharmaceutical composition further comprises a pharmaceutically acceptable carrier. The pharmaceutically acceptable carrier can be selected from any or a combination of: a diluent, a bulking agent, a solubilizer, a binder, a disintegrant, a chelating agent, a glidant, a flavoring agent, a coloring agent, a tonicity agent, a sweetening agent, a buffering agent, a preservative, a lubricant, an emulsifier, a suspending agent, and a solvent.

In some embodiments, the diluent(s) include(s), but not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, and mixtures thereof.

In some embodiments, the bulking agent(s) include(s), but not limited to, lactose USP, Starch 1500, mannitol, sorbitol, maltodextrin, maltitol or other non-reducing sugars; microcrystalline cellulose (e.g., Avicel), dibasic calcium phosphate (anhydrous or dihydrate), sucrose, and mixtures thereof.

In some embodiments, the solubilizer(s) include(s), but not limited to, propylene glycol, oil, castor oil, Beeswax, d-alpha-tocopherol, alpha-cyclodextrin, beta-cyclodextrin, Hydrogenated soy phosphatidylcholine, I-alpha-dimyristoyl phosphatidylglycerol, and mixtures thereof.

In some embodiments, the binder(s) include(s), but not limited to, hypromellose (or hypromellose 5 cps), polyvinyl pyrrolidone, copolymers of vinyl pyrrolidone with other vinyl derivatives, hydroxypropyl cellulosic derivatives (such as methylcellulose, carboxymethyl cellulose, hydroxyethyl cellulose, hydroxyethylmethyl cellulose, hydroxypropylcellulose etc), polyacrylates (such as Carbopol, polycarbophil, etc), povidone (all grades), polyox of any molecular weight or grade, irradiated or not, maize starch, povidone, copovidone, corn starch, starch, polyvinylpyrrolidone (PVP), microcrystalline cellulose, powdered acacia, gelatin, guar gum, carbomer such as carbopol, polymethacrylates, starch, and mixtures thereof.

In some embodiments, disintegrant(s) include(s), but not limited to, croscarmellose sodium, sodium starch glyconate, citric acid, calcium carbonate, pregelatinized starch, and mixtures thereof.

In some embodiments, chelating agent(s) include(s), but not limited to, tetrasodium glutamate diacetate (e.g., Dissolvine GL-47-S), EDTA salt, and mixtures thereof.

In some embodiments, glidant(s) include(s), but not limited to, colloidal silicon dioxide, precipitated silicon dioxide, stearic acid, talk, aluminum silicate, fumed silica (CAB-O-SIL M-5P, trademark of Cabot Corporation), stearowet and sterotex, silicas (such as SILOID and SILOX silicas—trademarks of Grace Davison Products, Aerosil—trademark of Degussa Pharma), higher fatty acids and metal salts thereof, hydrogenated vegetable oils, and mixtures thereof.

In some embodiments, flavoring agent(s) include(s), but not limited to, fruit aromas such as orange, banana, strawberry, cherry, wild cherry, lemon; cardamom, anis, mint, menthol, vanillin, ethyl vanillin, and mixtures thereof.

In some embodiments, coloring agent(s) include(s), but not limited to, E102 Tartrazine, E104 Quin-oline Yellow, E110 Sunset Yellow FCF, E120—Cochineal, carminic acid, Carmines, E122 Azorubine (Carmoisine), E123 Amaranth, E124 Ponceau 4R (Cochineal Red A), E127 Erythrosine, E129 Allura Red, E131 Patent Blue, and mixtures thereof.

In some embodiments, tonicity agent(s) include(s), but not limited to, dextrose, glycerin, mannitol, potassium chloride, sodium chloride, and mixtures thereof.

In some embodiments, sweetening agent(s) include(s), but not limited to, sucralose, acesulfame-K, aspartame, saccharine or saccharine sodium and calcium salts, sodium cyclamate, sucrose, fructose, glucose, sorbitol, and mixtures thereof.

In some embodiments, the buffering agent(s) include(s), but not limited to, sodium citrate, potassium citrate, sodium citrate di-hydrate, citric acid, citric acid monohydrate, sodium bicarbonate, potassium bicarbonate, sodium di-hydrogen phosphate, potassium di-hydrogen phosphate, and mixtures thereof.

In some embodiments, preservative(s) include(s), but not limited to, p-hydroxybenzoic acid esters, sorbic acid, benzoic acid, propionic acid, or salts thereof, alcohols such as benzyl alcohol, butanol or ethanol, isopropyl alcohol and quaternary ammonium compounds such as benzalkonium chloride, sodium benzoate, and mixture thereof.

In some embodiments, lubricant(s) include(s), but not limited to, zinc stearate, magnesium stearate, stearic acid, calcium stearate, and mixture thereof.

In some embodiments, the emulsifier(s) include(s), but not limited to, ionic or non-ionic surfactants and emulsifiers, poloxamers, polyethylene glycols, polyethylene glycol monostearate, polysorbates, sodium lauryl sulfate, polyethoxylated, hydrogenated castor oil, and mixtures thereof.

In some embodiments, the suspending agent(s) include(s), but not limited to, microcrystalline cellulose, sodium carboxymethyl cellulose, hydroxyl propyl methylcellulose (HPMC), xanthan gum, acacia, tragacanth, alginates, guar gum, and colloidal silicon dioxide and mixtures thereof.

In some embodiments, solvent(s) include(s), but not limited to, methanol, ethanol, n-propanol, isopropanol, hexane, heptane, petroleum ether, cyclohexane, diethyl ether, diisopropyl ether, ethyl acetate, methyl acetate, ethyl formate, methyl formate, isobutyl acetate, n-butyl acetate, methylene chloride, ethylene chloride, chloroform, carbon tetrachloride, acetone, ethyl methyl ketone, di-isobutyl ketone, methyl isobutyl ketone, 1,4-dioxane, toluene, ammonia solution, glacial acetic acid, ammonium hydroxide, sodium hydroxide, calcium hydroxide, calcium carbonate, potassium hydroxide, potassium carbonate, water, and mixture thereof.

Another aspect of the present disclosure relates to use of an antioxidant for alleviation, prevention or treatment of one or more adverse effects of a cholinesterase inhibitor in a subject in need thereof.

In some embodiments, the cholinesterase inhibitor can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

In some embodiments, the antioxidant can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is N-acetylcysteine or a salt thereof. In some embodiments, the antioxidant is N-acetylcysteine. In some embodiments, the antioxidant is alpha-lipoic acid or a salt thereof. In some embodiments, the antioxidant is danthron or a salt thereof.

In some embodiments, the antioxidant, for use in alleviation, prevention or treatment of one or more adverse effects of the cholinesterase inhibitor, is selected from any or a combination of: N-acetylcysteine, alpha-lipoic acid, danthron, vitamin E, or a salt thereof. In some embodiments, the cholinesterase inhibitor is any or a combination of: donepezil, galantamine, rivastigmine or a salt thereof.

In some embodiments, N-acetylcysteine is used in alleviation, prevention or treatment of one or more adverse effects of donepezil in a subject in need thereof. In some embodiments, N-acetylcysteine is used in alleviation, prevention or treatment of one or more adverse effects of donepezil hydrochloride in a subject in need thereof.

The present disclosure relates to a method for preventing or treating a brain disease, the method comprising administering a combination of a cholinesterase inhibitor and an antioxidant to a subject in need thereof.

The cholinesterase inhibitor useful in the method for preventing or treating the brain disease can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful in the method for preventing or treating the brain disease can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine (NAC), alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the brain diseases include, but are not limited to, an ischemia disease, Alzheimer's disease, and dementia. The ischemia disease can be stroke, cerebral hemorrhage, cerebral infarction, head trauma, cerebral circulatory metabolic disorder, vascular dementia, or cerebral functional coma.

The present disclosure further relates to a method for preventing or treating an ischemia disease, the method comprising administering a combination of a cholinesterase inhibitor and an antioxidant to a subject in need thereof.

In some embodiments, the ischemia disease, without any limitation, can be one or more of: stroke, cerebral hemorrhage, cerebral infarction, head trauma, cerebral circulatory metabolic disorder, vascular dementia, and cerebral functional coma.

The cholinesterase inhibitor useful in the method for preventing or treating the ischemia disease can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful in the method for preventing or treating the ischemia disease can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the cholinesterase inhibitor can be selected from any or a combination of: donepezil, galantamine, rivastigmine or a salt thereof. In some embodiments, the antioxidant can be selected from any or a combination of: N-acetylcysteine, alpha-lipoic acid, danthron, vitamin E, or a salt thereof.

In some embodiments, the method for preventing or treating the ischemia disease comprising administering donepezil or a salt thereof, and N-acetylcysteine or a salt thereof. In some embodiments, the method comprising administering donepezil and N-acetylcysteine. In some embodiments, the method comprising administering donepezil hydrochloride and N-acetylcysteine.

In some embodiments, the method comprises administration of an antioxidant before, simultaneously with, or after administration of the cholinesterase inhibitor. In some embodiments, the cholinesterase inhibitor and the antioxidant are administered as a pharmaceutical composition or a formulation.

In some embodiments, the composition is a pharmaceutical composition for preventing or treating the ischemia disease. In some embodiments, the composition is a food composition for preventing the ischemia disease.

In some embodiments, the pharmaceutical composition further comprises a pharmaceutically acceptable carrier. The pharmaceutically acceptable carrier can be selected from any or a combination of: a diluent, a bulking agent, a solubilizer, a binder, a disintegrant, a chelating agent, a glidant, a flavouring agent, a colouring agent, a tonicity agent, a sweetening agent, a buffering agent, a preservative, a lubricant, an emulsifier, a suspending agent, and a solvent.

In some embodiments, the composition comprises donepezil or a salt thereof, and N-acetylcysteine or a salt thereof. In some embodiments, the composition comprises donepezil and N-acetylcysteine. In some embodiments, the composition comprises donepezil hydrochloride and N-acetylcysteine.

The present disclosure further relates to a combination of a cholinesterase inhibitor and an antioxidant for use in prevention or treatment of an ischemia disease in a subject in need thereof.

The cholinesterase inhibitor useful for preventing or treating the ischemia disease can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful for preventing or treating the ischemia disease can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, cholinesterase inhibitor useful for preventing or treating the ischemia disease can be selected from any or a combination of: donepezil, galantamine, rivastigmine or a salt thereof. In some embodiments, the antioxidant useful for preventing or treating the ischemia disease can be selected from any or a combination of: N-acetylcysteine, alpha-lipoic acid, danthron, vitamin E, or a salt thereof.

In some embodiments, the antioxidant is administered before, simultaneously with, or after administration of the cholinesterase inhibitor. In some embodiments, the cholinesterase inhibitor and the antioxidant are administered as a pharmaceutical composition or a formulation.

In some embodiments, the composition is a pharmaceutical composition for preventing or treating the neurodegenerative disease. In some embodiments, the composition is a food composition useful for prevention of the neurodegenerative disease.

In some embodiments, the pharmaceutical composition for preventing or treating the neurodegenerative disease comprises donepezil or a salt thereof, and N-acetylcysteine or a salt thereof. In some embodiments, the pharmaceutical composition for preventing or treating the neurodegenerative disease comprises donepezil and N-acetylcysteine. In some embodiments, the pharmaceutical composition comprises donepezil hydrochloride and N-acetylcysteine.

The present disclosure further relates to a method for preventing or treating a neurodegenerative disease, the method comprising administrating a combination of a cholinesterase inhibitor and an antioxidant to a subject in need thereof.

In some embodiments, the cholinesterase inhibitor useful in the method for preventing or treating the neurodegenerative disease can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

In some embodiments, the antioxidant useful in the method for preventing or treating the neurodegenerative disease can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the cholinesterase inhibitor can be selected from any or a combination of: donepezil, galantamine, rivastigmine or a salt thereof. In some embodiments, the antioxidant can be selected from any or a combination of: N-acetylcysteine, alpha-lipoic acid, danthron, vitamin E, or a salt thereof.

In some embodiments, the method for preventing or treating the neurodegenerative disease comprising administering donepezil or a salt thereof, and N-acetylcysteine or a salt thereof. In some embodiments, the method comprising administering donepezil and N-acetylcysteine. In some embodiments, the method comprising administering donepezil hydrochloride and N-acetylcysteine.

In some embodiments, the method comprising administration of an antioxidant before, simultaneously with, or after administration of the cholinesterase inhibitor. In some embodiments, the cholinesterase inhibitor and the antioxidant are administered as a pharmaceutical composition or a formulation.

In some embodiments, the composition is a pharmaceutical composition for preventing or treating the neurodegenerative disease. In some embodiments, the composition is a food composition for preventing the neurodegenerative disease.

In some embodiments, the pharmaceutical composition further comprises a pharmaceutically acceptable carrier. The pharmaceutically acceptable carrier can be selected from any or a combination of: a diluent, a bulking agent, a solubilizer, a binder, a disintegrant, a chelating agent, a glidant, a flavoring agent, a coloring agent, a tonicity agent, a sweetening agent, a buffering agent, a preservative, a lubricant, an emulsifier, a suspending agent, and a solvent.

In some embodiments, the composition comprises donepezil or a salt thereof, and N-acetylcysteine or a salt thereof. In some embodiments, the composition comprises donepezil and N-acetylcysteine. In some embodiments, the composition comprises donepezil hydrochloride and N-acetylcysteine.

The present disclosure further relates to a combination of a cholinesterase inhibitor and an antioxidant for use in prevention or treatment of neurodegenerative disease in a subject in need thereof.

In some embodiments, the neurodegenerative disease, without limitation, can be selected from the group consisting of: Alzheimer's disease, Parkinson's disease, dementia, cognitive dysfunction, progressive supranuclear palsy, multiple system atrophy, olive-pontine-cerebellar atrophy (OPCA), Shy-Drager syndrome, striatal-substantia nigra degeneration, Huntington's disease, amyotrophic lateral sclerosis (ALS), essential tremor, cortico-basal ganglia degeneration, diffuse Lewy body disease, Parkinson-ALS-dementia complex, Niemann-Pick disease and Pick disease.

The cognitive dysfunction is deeply related to aging, may include without limitation any disease in which abnormal nerve cell death occurs rapidly in a part of the nervous system or in the entire brain, resulting in loss of function of the brain and spinal cord, thereby reducing cognitive ability, unlike the normal aging process. Non-limiting examples of the cognitive dysfunction may include mild cognitive impairment, Alzheimer's disease, frontotemporal dementia, Lewy body disease, cortico-basal ganglia degeneration, learning disabilities, agnosia, amnesia, aphasia, apraxia and delirium.

The present disclosure also relates to a method for preventing or treating Alzheimer's disease, the method comprising administering a combination of a cholinesterase inhibitor and an antioxidant to a subject in need thereof. The cholinesterase inhibitor useful in the method for preventing or treating the Alzheimer's disease can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful in the method for preventing or treating the Alzheimer's disease can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the cholinesterase inhibitor can be selected from any or a combination of: donepezil, galantamine, rivastigmine or a salt thereof. In some embodiments, the antioxidant can be selected from any or a combination of: N-acetylcysteine, alpha-lipoic acid, danthron, vitamin E, or a salt thereof.

In some embodiments, the method for preventing or treating the Alzheimer's disease comprising administering donepezil or a salt thereof, and N-acetylcysteine or a salt thereof. In some embodiments, the method comprising administering donepezil and N-acetylcysteine. In some embodiments, the method comprising administering donepezil hydrochloride and N-acetylcysteine.

In some embodiments, the method comprising administration of an antioxidant before, simultaneously with, or after administration of the cholinesterase inhibitor. In some embodiments, the cholinesterase inhibitor and the antioxidant are administered as a pharmaceutical composition or a formulation.

In some embodiments, the composition is a pharmaceutical composition for preventing or treating the Alzheimer's disease. In some embodiments, the composition is a food composition for preventing the Alzheimer's disease.

In some embodiments, the pharmaceutical composition further comprises a pharmaceutically acceptable carrier. The pharmaceutically acceptable carrier can be selected from any or a combination of: a diluent, a bulking agent, a solubilizer, a binder, a disintegrant, a chelating agent, a glidant, a flavoring agent, a coloring agent, a tonicity agent, a sweetening agent, a buffering agent, a preservative, a lubricant, an emulsifier, a suspending agent, and a solvent.

In some embodiments, the composition comprises donepezil or a salt thereof, and N-acetylcysteine or a salt thereof. In some embodiments, the composition comprises donepezil and N-acetylcysteine. In some embodiments, the composition comprises donepezil hydrochloride and N-acetylcysteine.

The present disclosure also relates to a combination of a cholinesterase inhibitor and an antioxidant for use in prevention or treatment of Alzheimer's disease in a subject in need thereof.

The cholinesterase inhibitor useful in the method for preventing or treating the Alzheimer's disease can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride. The antioxidant useful in the method for preventing or treating the Alzheimer's disease can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

The present disclosure also relates to a method for preventing or treating dementia, the method comprising administering a combination of cholinesterase inhibitor and an antioxidant to a subject in need thereof.

The cholinesterase inhibitor useful in the method for preventing or treating the dementia can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful in the method for preventing or treating the dementia disease can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the cholinesterase inhibitor can be selected from any or a combination of: donepezil, galantamine, rivastigmine or a salt thereof. In some embodiments, the antioxidant can be selected from any or a combination of: N-acetylcysteine, alpha-lipoic acid, danthron, vitamin E, or a salt thereof.

In some embodiments, the method for preventing or treating dementia comprising administering donepezil or a salt thereof, and N-acetylcysteine or a salt thereof. In some embodiments, the method comprising administering donepezil and N-acetylcysteine. In some embodiments, the method comprising administering donepezil hydrochloride and N-acetylcysteine.

In some embodiments, the method comprising administration of an antioxidant before, simultaneously with, or after administration of the cholinesterase inhibitor.

In some embodiments, the cholinesterase inhibitor and the antioxidant is administered as a pharmaceutical composition or a formulation.

In some embodiments, the composition is a pharmaceutical composition for preventing or treating dementia. In some embodiments, the composition is a food composition for preventing dementia.

In some embodiments, the pharmaceutical composition further comprises a pharmaceutically acceptable carrier. The pharmaceutically acceptable carrier can be selected from any or a combination of: a diluent, a bulking agent, a solubilizer, a binder, a disintegrant, a chelating agent, a glidant, a flavouring agent, a colouring agent, a tonicity agent, a sweetening agent, a buffering agent, a preservative, a lubricant, an emulsifier, a suspending agent, and a solvent.

In some embodiments, the composition comprises donepezil or a salt thereof, and N-acetylcysteine or a salt thereof. In some embodiments, the composition comprises donepezil and N-acetylcysteine. In some embodiments, the composition comprises donepezil hydrochloride and N-acetylcysteine.

The present disclosure also relates to a combination of a cholinesterase inhibitor and an antioxidant for use in prevention or treatment of dementia in a subject in need thereof.

The cholinesterase inhibitor useful for preventing or treating the dementia can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful for preventing or treating the dementia can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

The present disclosure further relates to a method for promoting neuronal differentiation, the method comprising administering a combination of a cholinesterase inhibitor and an antioxidant to a subject in need thereof.

The cholinesterase inhibitor useful in the method for promoting neuronal differentiation can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful in the method for promoting neuronal differentiation can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the method for promoting neuronal differentiation comprises administering donepezil or a salt thereof, and N-acetylcysteine or a salt thereof. In some embodiments, the method comprises administering donepezil and N-acetylcysteine. In some embodiments, the method comprising administering donepezil hydrochloride and N-acetylcysteine.

The present disclosure further relates to a combination of a cholinesterase inhibitor and an antioxidant for use in promoting neuronal differentiation in a subject in need thereof.

The cholinesterase inhibitor useful in promoting neuronal differentiation can be selected from any or a combination of: 7-methoxytacrine, albameline, ambenonium, anseculin, arecoline, cevimeline, citicoline, demacarium, donepezil, edrophonium, eptastigmine, fasciculin, heptyl-physostigmine, huperzine A and its analogues, icopezil, ipidacrine, linopiridine, metrifonate, milameline, neostigmine, nomeostigmine, pyridostigmine, norpyridostigmine, physostigmine, rivastigmine, subcomeline, suronacrine, tacrine analogues, tacrine, talsaclidine, velnacrine, xanomeline, itopride, acotiamide, huperzine, galanthamine and ziprasidone or a salt thereof. In some embodiments, the cholinesterase inhibitor can be selected from any or a combination of: donepezil, galantamine, rivastigmine or a salt thereof. In some embodiments, the cholinesterase inhibitor is donepezil or a salt thereof. In some embodiments, the cholinesterase inhibitor is donepezil hydrochloride.

The antioxidant useful in promoting neuronal differentiation can be selected from any or a combination of: N-acetylcysteine, ascorbic acid (Vitamin C), alpha-lipoic acid, ellagic acid, scopoletin, forsythin, isoferulic acid, gamma-oryzanol, trans-anethole, thioctic acid, tiopronin, cysteamine, gallic acid, glutathione, salvianolic acid, secoisolariciresinol diglucoside, vitamin E, verbascoside, lappaconitine, selenium, coenzyme Q10, vitamin A, catechin, danthron, danthron, L-selenomethionine, ligustrazine, pinocembrin, or a salt thereof. In some embodiments, the antioxidant can be selected from any or a combination of: N-acetylcysteine, alpha-lipoic acid, danthron, vitamin E, or a salt thereof. In some embodiments, the antioxidant is alpha-lipoic acid or a salt thereof. In some embodiments, the antioxidant is danthron or a salt thereof. In some embodiments, the antioxidant is N-acetylcysteine or a salt thereof. In some embodiments, the antioxidant is N-acetylcysteine.

In some embodiments, the antioxidant is administered before, simultaneously with, or after administration of the cholinesterase inhibitor. In some embodiments, the cholinesterase inhibitor and the antioxidant are administered as a pharmaceutical composition or a formulation.

In some embodiments, the composition is a pharmaceutical composition. In some embodiments, the composition is a food composition.

In some embodiments, the composition for promoting neuronal differentiation comprises donepezil or a salt thereof, and N-acetylcysteine or a salt thereof. In some embodiments, the composition for promoting neuronal differentiation comprises donepezil and N-acetylcysteine. In some embodiments, the composition for promoting neuronal differentiation comprises donepezil hydrochloride and N-acetylcysteine.

In some embodiments, the pharmaceutical composition further comprises a pharmaceutically acceptable carrier. The pharmaceutically acceptable carrier can be selected from any or a combination of: a diluent, a bulking agent, a solubilizer, a binder, a disintegrant, a chelating agent, a glidant, a flavoring agent, a coloring agent, a tonicity agent, a sweetening agent, a buffering agent, a preservative, a lubricant, an emulsifier, a suspending agent, and a solvent.

In some embodiments, the pharmaceutical composition comprises a pharmaceutically effective amount of a combination of a cholinesterase inhibitor(s) and an antioxidant(s). In some embodiments, the pharmaceutical compositions comprise a pharmaceutically effective amount of a combination of a cholinesterase inhibitor and an antioxidant comprising a therapeutically effective amount of the cholinesterase inhibitor and an effective amount of the antioxidant. The pharmaceutically effective amount of the combination of a cholinesterase inhibitor and an antioxidant, the therapeutically effective amount of a cholinesterase inhibitor and/or the effective amount of an antioxidant can be readily determined based on factors such as the type of disease, the patient's age, weight, health, gender, the patient's sensitivity to the drug, the route of administration, the method of administration, the number of doses, the duration of treatment, and the drugs used in combination or concurrently.

In some embodiments, the cholinesterase inhibitor and the antioxidant may be combined in a molar ratio of about 1:0.1 to 2000, about 1:0.1 to 1500, about 1:1 to 1500, about 1:1 to 1000, about 1:1 to 500, about 1:1 to 400, about 1:1 to 350, about 1:1 to 300, about 1:1 to 290, about 1:1 to 280, about 1:1 to 270, about 1:1 to 260, about 1:1 to 250, about 1:1 to 240, about 1:1 to 230, about 1:1 to 220, about 1:1 to 220, about 1:1 to 210, about 1:1 to 200, about 1:1 to 190, about 1:1 to 180, about 1:1 to 170, about 1:1 to 160, about 1:1 to 150, about 1:1 to 140, about 1:1 to 130, about 1:1 to 120, about 1:1 to 110, about 1:1 to 100, about 1:1 to 90, about 1:1 to 80, about 1:1 to 70, about 1:1 to 60, about 1:1 to 50, about 1:1 to 40, about 1:1 to 30, about 1:1 to 20, about 1:1-10, about 1:30 to 2000, about 1:30 to 1500, about 1:30 to 1000, about 1:30 to 500, about 1:30 to 400, about 1:30 to 350, about 1:30 to 300, about 1:30 to 290, about 1:30 to 280, about 1:30 to 270, about 1:30 to 260, about 1:30 to 250, about 1:30 to 240, about 1:30 to 230, about 1:30 to 220, about 1:30 to 210, about 1:30 to 200, about 1:30 to 190, about 1:30 to 180, about 1:30 to 170, about 1:30 to 160, about 1:30 to 150, about 1:30 to 140, about 1:30 to 130, about 1:30 to 120, about 1:30 to 110, about 1:30 to 100, about 1:30 to 90, about 1:30 to 80, about 1:30 to 70, about 1:30 to 60, about 1:30 to 50, about 1:30 to 40, about 1:60 to 2000, about 1:60 to 1500, about 1:60 to 1000, about 1:60 to 500, about 1:60 to 400, about 1:60 to 350, about 1:60 to 300, about 1:60 to 290, about 1:60 to 280, about 1:60 to 270, about 1:60 to 260, about 1:60 to 250, about 1:60 to 240, about 1:60 to 230, about 1:60 to 220, about 1:60 to 210, about 1:60 to 200, about 1:60 to 190, about 1:60 to 180, about 1:60 to 170, about 1:60 to 160, about 1:60 to 150, about 1:60 to 140, about 1:60 to 130, about 1:60 to 120, about 1:60 to 110, about 1:60 to 100, about 1:60 to 90, about 1:60 to 80, about 1:60 to 70, about 1:90 to 2000, about 1:90 to 1500, about 1:90 to 1000, about 1:90 to 500, about 1:90 to 400, about 1:90 to 350, about 1:90 to 300, about 1:90 to 290, about 1:90 to 280, about 1:90 to 270, about 1:90 to 260, about 1:90 to 250, about 1:90 to 240, about 1:90 to 230, about 1:90 to 220, about 1:90 to 210, about 1:90 to 200, about 1:90 to 190, about 1:90 to 180, about 1:90 to 170, about 1:90 to 160, about 1:90 to 150, about 1:90 to 140, about 1:90 to 130, about 1:90 to 120, about 1:90 to 110, about 1:90 to 100, about 1:120 to 2000, about 1:120 to 1500, about 1:120 to 1000, about 1:120 to 500, about 1:120 to 400, about 1:120 to 350, about 1:120 to 300, about 1:120 to 290, about 1:120 to 280, about 1:120 to 270, about 1:120 to 260, about 1:120 to 250, about 1:120 to 240, about 1:120 to 230, about 1:120 to 220, about 1:120 to 210, about 1:120 to 200, about 1:120 to 190, about 1:120 to 180, about 1:120 to 170, about 1:120 to 160, about 1:120 to 150, about 1:120 to 140, about 1:120 to 130, about 1:150 to 2000, about 1:150 to 1500, about 1:150 to 1000, about 1:150 to 500, about 1:150 to 400, about 1:150 to 350, about 1:150 to 300, about 1:150 to 290, about 1:150 to 280, about 1:150 to 270, about 1:150 to 260, about 1:150 to 250, about 1:150 to 240, about 1:150 to 230, about 1:150 to 220, about 1:150 to 210, about 1:150 to 200, about 1:150 to 190, about 1:150 to 180, about 1:150 to 170, about 1:150 to 160, about 1:180 to 2000, about 1:180 to 1500, about 1:180 to 1000, about 1:180 to 500, about 1:180 to 400, about 1:180 to 350, about 1:180 to 300, about 1:180 to 290, about 1:180 to 280, about 1:180 to 270, about 1:180 to 260, about 1:180 to 250, about 1:180 to 240, about 1:180 to 230, about 1:180 to 220, about 1:180 to 210, about 1:180 to 200, about 1:180 to 190, about 1:210 to 2000, about 1:210 to 1500, about 1:210 to 1000, about 1:210 to 500, about 1:210 to 400, about 1:210 to 350, about 1:210 to 300, about 1:210 to 290, about 1:210 to 280, about 1:210 to 270, about 1:210 to 260, about 1:210 to 250, about 1:210 to 240, about 1:210 to 230, about 1:210 to 220, about 1:240 to 2000, about 1:240 to 1500, about 1:240 to 1000, about 1:240 to 500, about 1:240 to 400, about 1:240 to 350, about 1:240 to 300, about 1:240 to 290, about 1:240 to 280, about 1:240 to 270, about 1:240 to 260, or about 1:240 to 250.

The composition can be administered to the subject in need thereof by any conventional route of administration, including, but not limited to, intravenous, intramuscular, oral, subcutaneous, intradermal, injections, drip injections, and parenteral.

The composition can be administered to the subject in need thereof as daily dose, or it is being possible to give the daily dose as single dose or in divided doses distributed over the day, preferably 1-3 dosages. The composition can be administered to the subject in need thereof for 1 to 90 days or more. Further, the subject may receive the specific dosage over a period of weeks, months, or years. For example, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years and the like. The choice of appropriate dosages for the drugs used either alone or in combination therapy according to the present disclosure can be determined and optimized by the skilled artisan, e.g., by observation of the subject, including the patient's overall health, the response to the therapy, and the like. Optimization, for example, may be necessary if it is determined that a subject is not exhibiting the desired therapeutic effect or conversely, if the subject is experiencing undesirable or adverse side effects that are too many in number or are of a troublesome severity.

The pharmaceutical compositions of the present disclosure comprise a pharmaceutically acceptable carrier. The pharmaceutically acceptable carrier can be selected from any or a combination of: a diluent, a bulking agent, a solubilizer, a binder, a disintegrant, a chelating agent, a glidant, a flavoring agent, a coloring agent, a tonicity agent, a sweetening agent, a buffering agent, a preservative, a lubricant, an emulsifier, a suspending agent, and a solvent.

In some embodiments, the diluent(s) include(s), but not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, and mixtures thereof.

In some embodiments, the bulking agent(s) include(s), but not limited to, lactose USP, Starch 1500, mannitol, sorbitol, maltodextrin, maltitol or other non-reducing sugars; microcrystalline cellulose (e.g., Avicel), dibasic calcium phosphate (anhydrous or dihydrate), sucrose, and mixtures thereof.

In some embodiments, the solubilizer(s) include(s), but not limited to, propylene glycol, oil, castor oil, Beeswax, d-alpha-tocopherol, alpha-cyclodextrin, beta-cyclodextrin, Hydrogenated soy phosphatidylcholine, I-alpha-dimyristoyl phosphatidylglycerol, and mixtures thereof.

In some embodiments, the binder(s) include(s), but not limited to, hypromellose (or hypromellose 5 cps), polyvinyl pyrrolidone, copolymers of vinyl pyrrolidone with other vinyl derivatives, hydroxypropyl cellulosic derivatives (such as methylcellulose, carboxymethyl cellulose, hydroxyethyl cellulose, hydroxyethyl methyl cellulose, hydroxypropylcellulose etc), polyacrylates (such as Carbopol, polycarbophil, etc), povidone (all grades), polyox of any molecular weight or grade, irradiated or not, maize starch, povidone, copovidone, corn starch, starch, polyvinylpyrrolidone (PVP), microcrystalline cellulose, powdered acacia, gelatin, guar gum, carbomer such as carbopol, polymethacrylates, starch, and mixtures thereof.

In some embodiments, disintegrant(s) include(s), but not limited to, croscarmellose sodium, sodium starch glyconate, citric acid, calcium carbonate, pregelatinized starch, and mixtures thereof.

In some embodiments, chelating agent(s) include(s), but not limited to, tetrasodium glutamate diacetate (e.g., Dissolvine GL-47-S), EDTA salt, and mixtures thereof.

In some embodiments, glidant(s) include(s), but not limited to, colloidal silicon dioxide, precipitated silicon dioxide, stearic acid, talk, aluminum silicate, fumed silica (CAB-O-SIL M-5P, trademark of Cabot Corporation), stearowet and sterotex, silicas (such as SILOID and SILOX silicas—trademarks of Grace Davison Products, Aerosil—trademark of Degussa Pharma), higher fatty acids and metal salts thereof, hydrogenated vegetable oils, and mixtures thereof.

In some embodiments, flavoring agent(s) include(s), but not limited to, fruit aromas such as orange, banana, strawberry, cherry, wild cherry, lemon; cardamom, anis, mint, menthol, vanillin, ethyl vanillin, and mixtures thereof.

In some embodiments, coloring agent(s) include(s), but not limited to, E102 Tartrazine, E104 Quin-oline Yellow, E110 Sunset Yellow FCF, E120—Cochineal, carminic acid, Carmines, E122 Azorubine (Carmoisine), E123 Amaranth, E124 Ponceau 4R (Cochineal Red A), E127 Erythrosine, E129 Allura Red, E131 Patent Blue, and mixtures thereof.

In some embodiments, tonicity agent(s) include(s), but not limited to, dextrose, glycerin, mannitol, potassium chloride, sodium chloride, and mixtures thereof.

In some embodiments, sweetening agent(s) include(s), but not limited to, sucralose, acesulfame-K, aspartame, saccharine or saccharine sodium and calcium salts, sodium cyclamate, sucrose, fructose, glucose, sorbitol, and mixtures thereof.

In some embodiments, the buffering agent(s) include(s), but not limited to, sodium citrate, potassium citrate, sodium citrate di-hydrate, citric acid, citric acid monohydrate, sodium bicarbonate, potassium bicarbonate, sodium di-hydrogen phosphate, potassium di-hydrogen phosphate, and mixtures thereof.

In some embodiments, preservative(s) include(s), but not limited to, p-hydroxybenzoic acid esters, sorbic acid, benzoic acid, propionic acid, or salts thereof, alcohols such as benzyl alcohol, butanol or ethanol, isopropyl alcohol and quaternary ammonium compounds such as benzalkonium chloride, sodium benzoate, and mixture thereof.

In some embodiments, lubricant(s) include(s), but not limited to, zinc stearate, magnesium stearate, stearic acid, calcium stearate, and mixture thereof.

In some embodiments, the emulsifier(s) include(s), but not limited to, ionic or non-ionic surfactants and emulsifiers, poloxamers, polyethylene glycols, polyethylene glycol monostearate, polysorbates, sodium lauryl sulfate, polyethoxylated, hydrogenated castor oil, and mixtures thereof.

In some embodiments, the suspending agent(s) include(s), but not limited to, microcrystalline cellulose, sodium carboxymethyl cellulose, hydroxyl propyl methylcellulose (HPMC), xanthan gum, acacia, tragacanth, alginates, guar gum, and colloidal silicon dioxide and mixtures thereof.

In some embodiments, solvent(s) include(s), but not limited to, methanol, ethanol, n-propanol, isopropanol, hexane, heptane, petroleum ether, cyclohexane, diethyl ether, diisopropyl ether, ethyl acetate, methyl acetate, ethyl formate, methyl formate, isobutyl acetate, n-butyl acetate, methylene chloride, ethylene chloride, chloroform, carbon tetrachloride, acetone, ethyl methyl ketone, di-isobutyl ketone, methyl isobutyl ketone, 1,4-dioxane, toluene, ammonia solution, glacial acetic acid, ammonium hydroxide, sodium hydroxide, calcium hydroxide, calcium carbonate, potassium hydroxide, potassium carbonate, water, and mixture thereof.

Depending on the intended mode of administration, the pharmaceutical composition may be formulated as a solid, semi-solid or liquid dosage form. The composition may be incorporated into convenient dosage forms such as capsules, tablets, or injectable preparations.

The compositions and/or formulations of the present disclosure may be formulated to achieve a therapeutic effect as a modified releases dosage form such as immediate release, controlled release, sustained release, and extended-release formulations thereof.

Non-limiting examples of dosage forms includes tablet, lozenge, capsule, caplet, modified release tablet or lozenge, troches, elixirs, suspension, solution, emulsion, suppository, granules, pellets, beads, powder, wafer, aerosol sprays (oral, nasal, dermal), cream, ointment, lotion, patches, powders such as a sterile packaged powder, a dispensable powder, and an effervescent powder, pre-filled syringe, pre-filled pen, gel, tablet in tablet, bilayer tablet, trilayer tablet, inlay tablet, capsule in capsule, tablet(s) in capsule, granules and/or pellets in capsule, pellets and tablet in capsules and the likes. However, any or a combination of pharmaceutical dosage form(s), as known to or appreciated by a person skilled in the art, can be utilized to serve the intended purpose.

In the case of injectables, it can be prepared in single-dose ampoules or multiple-dose formulations as an aqueous or nonaqueous liquid suspension. In some embodiments, the injectable formulation can be prepared using an aqueous solvent, such as saline or intravenous solution, a non-aqueous solvent, such as a vegetable oil, a higher fatty acid ester (e.g., oleic acid ethyl), an alcohol (e.g., ethanol, benzyl alcohol, propylene glycol, or glycerin), etc, and included in pharmaceutical carriers such as stabilizers to prevent spoilage (e.g., ascorbic acid, sodium hydrogen sulfite, sodium pyrosulfite, BHA, tocopherols, EDTA, etc.), emulsifiers, buffers to adjust pH, and preservatives to inhibit microbial growth (e.g., phenylmercury nitrate, thimerosal, benzalkonium chloride, phenol, cresol, benzyl alcohol, etc.). Examples of suitable carriers for injectables include, but are not limited to, solvents or dispersion media comprising water, ethanol, polyols (e.g., glycerol, propylene glycol, and liquid polyethylene glycol), mixtures thereof, and/or vegetable oils. More preferably, suitable carriers include Hanks' solution, Ringer's solution, phosphate buffered saline (PBS) containing triethanolamine, or isotonic solutions such as sterile water for injection, 10% ethanol, 40% propylene glycol, and 5% dextrose. To protect the injectable from microbial contamination, the injectable may additionally contain various antibacterial and antifungal agents such as parabens, chlorobutanol, phenols, sorbic acid, thimerosal, and the like. In addition, the injectable may further comprise an isotonic agent such as sugar or sodium chloride in most cases.

The food compositions of the present disclosure include all forms of functional foods, nutritional supplements, health foods, and food additives.

Food compositions of the above types can be prepared in various forms according to conventional methods known in the art. By way of example, but not limitation, the cholinesterase inhibitor and antioxidant can be liquefied, granulated, encapsulated, and powdered for consumption in the form of teas, juices, and drinks. In addition, donepezil and N-acetylcysteine can be formulated into compositions by mixing them with the active ingredients of the disclosure known to be effective against respective diseases. Furthermore, In addition, cholinesterase inhibitors and antioxidants can be added to beverages (including alcoholic beverages), fruits and their processed products (e.g., canned, bottled, jam, marmalade, etc.), fish, meat and their processed products (e.g., ham, sausage corned beef, etc.), breads and noodles (e.g., udon, soba, ramen, spaghetti, macaroni, etc.), fruit juices, various beverages, cookies, malt, dairy products (e.g., butter, cheese, etc.), edible vegetable oils, margarine, vegetable proteins, retort foods, frozen foods, various condiments (e.g., miso, soy sauce, sauces, etc.), etc. including, but not limited to, functional foods. In addition, cholinesterase inhibitors and antioxidants can be formulated in powder or concentrate form for use as additives.

Preferred amounts of cholinesterase inhibitors and antioxidant in the food compositions of the present disclosure include, but are not limited to, 0.1 to 90 wt % of the final prepared food product. More preferably, food compositions comprising the cholinesterase inhibitors and antioxidants of the present disclosure as active ingredients can be prepared in the form of a health functional food or dietary supplement, particularly in combination with active ingredients known to be effective against respective disease and/or condition.

EXAMPLES

The following Examples are provided to illustrate, not to limit, aspects of the present invention. Materials and reagents described in the Examples are commercially available unless otherwise specified. The following Examples illustrate that in certain embodiments of the invention the treatment with a combination of a cholinesterase inhibitor and an antioxidant shows a significant difference when compared to control (no treatment) or treatment with a cholinesterase inhibitor alone or an antioxidant alone. The following Examples illustrate that in certain embodiments of the invention the treatment with a combination of a cholinesterase inhibitor and an antioxidant shows a synergistic effect when compared to control.

Example 1

Effect of Antioxidant in Alleviating Adverse Effects of Cholinesterase Inhibitors To evaluate the effect of antioxidant in alleviating the adverse effects associated with administration of a cholinesterase inhibitor, Sprague-Dawley (SD) Female rats were used. Animals were macroscopically inspected and weighed at receipt. Then rats were acclimatized under laboratory conditions for 7 days and general clinical observations were made daily. The rats were housed and maintained at a temperature range of 22±3° C., relative humidity range of 55±15%, ventilation of 10-20 air changes/hour, 150-300 Lux of luminous intensity, and a 12-hour light/12-hour dark cycle (lighted 08:00-20:00).

Healthy rats were selected during the acclimatization period and were weighed. Rats with body weight closest to the mean were selected and randomly distributed in 5 group, such that each group had a comparable weight distribution. Donepezil HCl (DONE) and N-Acetylcysteine (NAC) were dissolved in sterile distilled water to prepare the daily dose as shown in Table 1 below and were refrigerated until further use. Each of groups were orally fed once a day for 4 weeks in a dose as shown in Table 1.

TABLE 1

Dosage regimen

| Groups | Number of animals | ID | Dose volume (mL/kg/day) | Dose (mg/kg/day) Donepezil HCl | NAC | Total |
|---|---|---|---|---|---|---|
| G1 | 5 | 1-5 | 20 | 0 | 0 | 0 |
| G2 | 5 | 6-10 | 20 | 20 | 400 | 420 |
| G3 | 5 | 11-15 | 20 | 20 | 1200 | 1220 |
| G4 | 5 | 16-20 | 20 | 20 | 2400 | 2420 |
| G5 | 5 | 21-25 | 20 | 20 | 0 | 20 |

The first day of administration was designated as Day 1. All rats were observed at least once daily for mortality and/or any clinical sign including the type of sign(s), date of occurrence, and severity of signs and were recorded individually. Body weight was measured on Day 1 (pre-dose) and subsequently weekly.

The various types of adverse effects of donepezil that may occur in rats and the types of adverse events that may occur in humans may be related as shown in Table 2.

TABLE 2

Adverse effects

| rats | human |
|---|---|
| flexibility | salivation |

TABLE 2-continued

| Adverse effects | |
|---|---|
| rats | human |
| prone position | extrapyramidal disorder, asthenia, drowsiness |
| decreased voluntary movement | extrapyramidal disorder, asthenia, drowsiness |
| shivering | extrapyramidal disorder, tremor |
| hypotonia | extrapyramidal disorder, asthenia, drowsiness |
| hypothermia | hypothermia |
| Pallor | Nausea, bradycardia, hypotension |
| miosis | miosis |
| Toe curling | extrapyramidal disorder, muscle spasm |

Decreased voluntary movement, hypotonia, hypothermia, and pallor are some common adverse effects caused by administration of cholinesterase inhibitors, and the same can be observed in FIG. 1.

Figure 2:
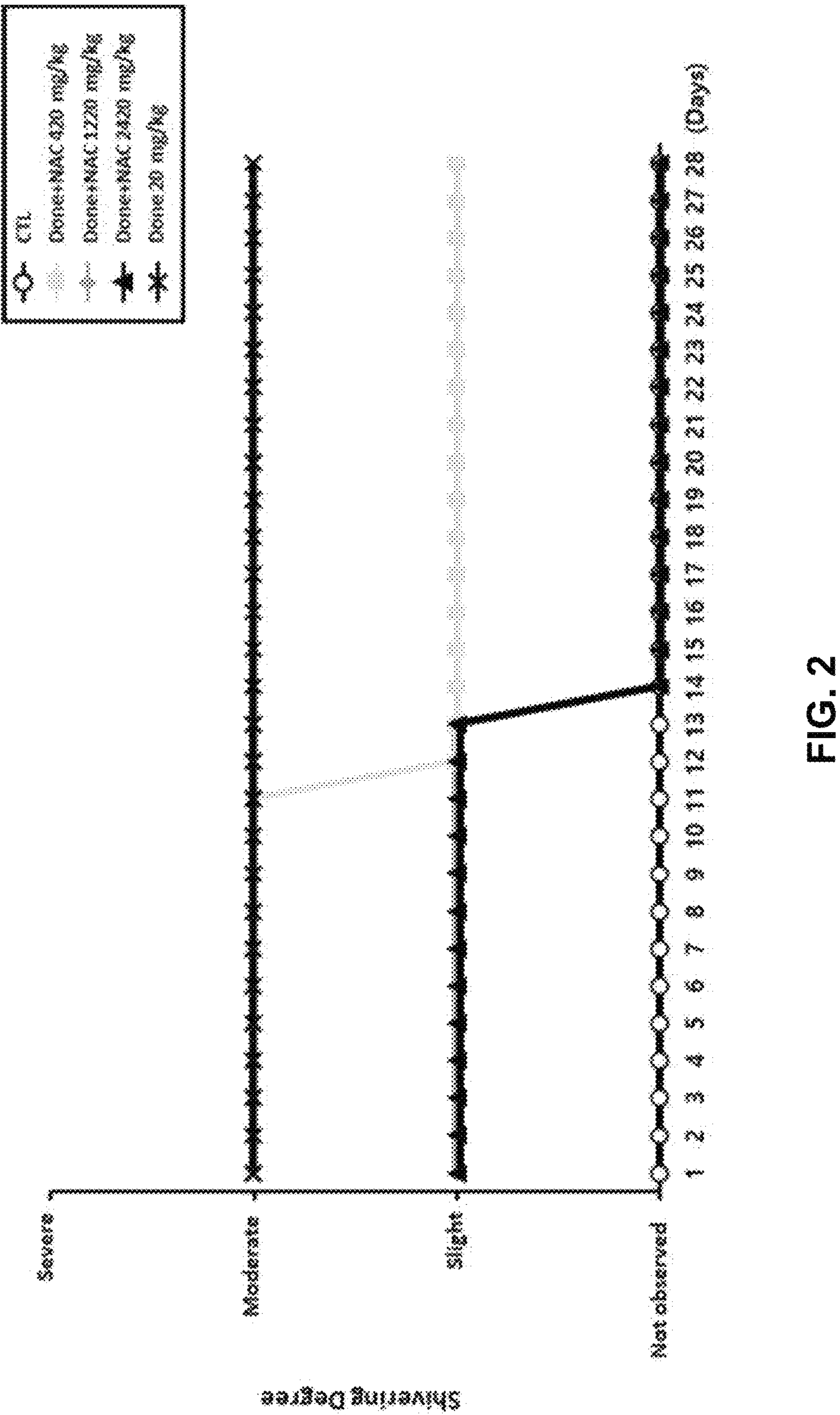
FIG. 2 illustrates the degree and duration of shivering (tremors) amongst the adverse effects caused by donepezil in female rats to which either donepezil alone or a combination of donepezil and N-acetylcysteine was administrated.

As seen from FIG. 1, hypotonia, hypothermia, and pallor symptoms were reduced in rats to whom a combination (DONE+NAC) comprising 20 mg/kg of donepezil HCl (DONE) and 1200 or 2400 mg/kg of NAC was administered, as compared to the rats treated with 20 mg/kg of donepezil HCl alone (DONE). Similarly, the decreased voluntary movement of rats treated with 20 mg/kg of donepezil HCl alone (DONE) was improved in rats administered with the combination (DONE+NAC) comprising 20 mg/kg of donepezil HCl (DONE) and 2400 mg/kg of NAC. A similar observation can be made in FIG. 2, wherein the degree and duration of shivering (tremors) caused by administration of 20 mg/kg of donepezil HCl (DONE) alone in rats, were reduced in rats administered with the combination (DONE+NAC) comprising 20 mg/kg of donepezil HCl (DONE) and any of 400, 1200, and 2400 mg/kg of NAC.

Example 2

Antioxidant Effect of Combination of Cholinesterase Inhibitor and Antioxidant In cerebrovascular diseases, ischemic stroke causes a large number of free radicals to be produced due to a reduced blood flow to the ischemic area, resulting in an accumulation of oxidized metabolites. These free radicals can cause oxidative stress, which can affect many organs, including brain cells. To minimize the damage from free radicals, cells activate antioxidants and antioxidant enzymes to remove free radical intermediates and inhibit oxidative reactions to defend cells and the body.

To investigate the antioxidant effect of the combination of donepezil HCl (DONE) and NAC, neuronal cells (SH-SY5Y) were treated with $H_2O_2$ to induce oxidative stress, and reactive oxygen species (ROS) production was measured after treatment with control, DONE alone (5 uM), NAC alone (5 uM), and combination of DONE (2.5 uM)+NAC (2.5 uM) (NDC).

SH-SY5Y cells were plated in 96 well plates at 2×105 cells/well in DMEM supplemented with 10% fetal bovine serum (FBS; YOUNG IN, US-FBS-500) and 1% penicillin-streptomycin (P-S; Gibco, 15070063). Six hours after seeding, SH-SY5Y cells were treated with 100 μM $H_2O_2$ for 24 hours (Sigma, #323381) followed by incubation with DONE alone, NAC alone, and combination of DONE and NAC. After incubation, ROS activity in the cell was measured by adding DCF-DA (Thermo, #D399) containing media. Absorbance was measured using a Synergy HTX Multi-Mode reader (Biotek) with 465 nm excitation and 540 nm emission. Measured fluorescence was normalized to control as follows: (drug-treated group OD–DCF-DA alone O.D)/(control O.D–DCF alone O.D)*100.

Figure 3:
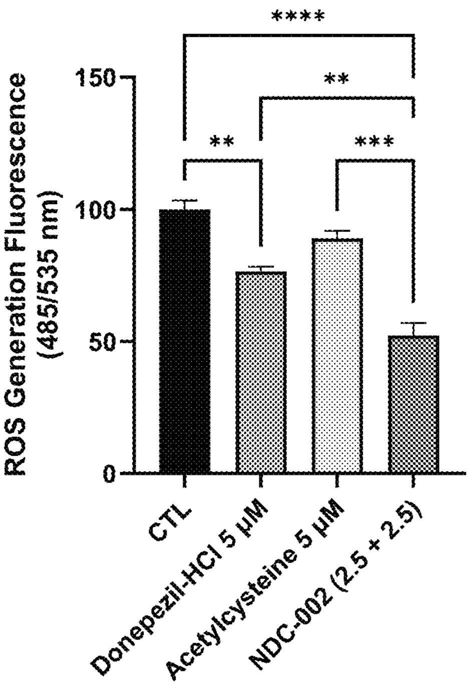
FIG. 3 illustrates the reduction in Reactive Oxygen Species (ROS) in nerve cells subjected to oxidative stress after treatment with donepezil alone, N-acetylcysteine alone, or a combination of donepezil and N-acetylcysteine.

As seen from FIG. 3, combination of donepezil HCl and NAC (NDC) significantly reduced the content of ROS in cells when compared with cells treated with donepezil HCl alone or NAC alone. (*P<0.05, P<0.01, **P<0.0001, one-way ANOVA). Additionally, the below Bliss Independence calculations show that the combination of NAC (antioxidant) and DONE (cholinesterase inhibitor) exhibits a synergistic effect in reducing ROS levels. The actual effect of NDC ($C_{NDC}$) in reducing the ROS levels is greater than the predicted response ($C_{bliss}$) calculated using Bliss Independence model.

Mean values from the graph shown in FIG. 3: CTL (100%), Donepezil-HCl (76.52%), NAC (88.93%), NDC (52.20%)

$$C_{Done}: CTL - \text{DONE} = 100\% - 76.52(\%) = 23.48(\%) = 0.2348$$

$$C_{NAC}: CTL - NAC = 100(\%) - 88.93(\%) = 11.07(\%) = 0.1107$$

$$C_{Bliss} = C_{Done} + C_{NAC} - C_{Done} * C_{NAC} = 0.2348 + 0.1107 - (0.2348 * 0.1107) = 0.3195$$

$$\text{Predicted response} = C_{Bliss} * 100 = 0.3195 * 100 = 31.95(\%)$$

$$C_{NDC}: CTL - NDC = 100(\%) - 52.20(\%) = 47.80(\%) = 0.478$$

$$\text{Bliss Value} = C_{NDC} - C_{Bliss} = 0.4780 - 0.3195 = 0.1585$$

Bliss value of NDC (0.1585) is greater than zero, indicating that the two drugs in the NDC are synergistic in exhibiting antioxidant effect.

Example 3

Anti-Inflammatory Effect of Combination of Cholinesterase Inhibitor and Antioxidant To investigate the anti-inflammatory effect microglia cells (BV2) were treated with LPS to induce an inflammatory reaction, and the expression of inflammatory marker IL-6 and production of nitric oxide (NO) was measured after treatment with donepezil HCl alone, NAC alone, and combination of donepezil HCl and NAC.

Briefly, BV2 microglial cells were plated in 96-well plates at 2×105 cells/well in DMEM high glucose medium (Welgene, LM001-05) supplemented with 10% fetal bovine serum (FBS; YOUNG IN, US-FBS-500) and 1% penicillin-streptomycin (P-S; Gibco, 15070063). Six hours after cell seeding, BV2 microglial cells were treated with 1 μg/ml LPS (Sigma, L4391) followed by treatment with donepezil HCl alone, NAC alone, and NDC, and incubated (37° C./5% CO2) for 18 hours.

IL-6 ELISA

After incubation, IL-6 levels were quantified from half of the cell media using mouse IL-6 ELISA kit (R&D systems, M60006). Colorimetric changes in the media and assay diluent were measured using a Synergy HTX Multi-Mode reader (Biotek) at 450 nm. As can be seen from FIG. 4, combination of donepezil HCl and NAC significantly reduced the content of IL-6 in cells when compared with cells treated with donepezil HCl alone or NAC alone. (*P<0.001, **P<0.0001, one-way ANOVA). Additionally, the below Bliss Independence calculations show that the combination of NAC (antioxidant) and donepezil HCl (cholinesterase inhibitor) exhibits a synergistic effect in reducing the content of IL-6. The actual effect of NDC ($C_{NDC}$) in reducing IL-6 levels is greater than the predicted response ($C_{Bliss}$) calculated using Bliss Independence model.

Figure 4:
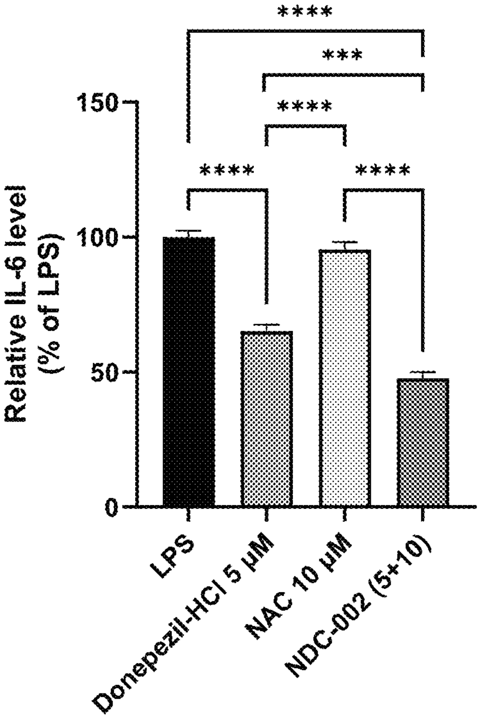
FIG. 4 illustrates the anti-inflammatory effect by measuring the level of Interleukin-6 (IL-6) in microglial cells (BV2 cell) treated with lipopolysaccharide (LPS), an inflammatory response inducing substance, after treatment with donepezil alone, N-acetylcysteine alone, or a combination of donepezil and N-acetylcysteine.

Mean values from the graph shown in FIG. 4: LPS (100%), Donepezil-HCl (65.12%), NAC (95.48%), NDC (47.71%)

$$C_{Done}: LPS - \text{DONE} = 100(\%) - 65.12(\%) = 34.88(\%) = 0.3488$$

$$C_{NAC}: LPS - NAC = 100(\%) - 95.48(\%) = 4.52(\%) = 0.0452$$

$$C_{Bliss} = C_{Done} + C_{NAC} - C_{done} * C_{NAC} = 0.3488 + 0.0452 - (0.3488 * 0.0452) = 0.3782$$

$$\text{Predicted response} = C_{Bliss} * 100 = 0.3782 * 100 = 37.82(\%)$$

$$C_{NDC}: LPS - NDC = 100(\%) - 47.71(\%) = 52.29(\%) = 0.5229$$

$$\text{Bliss value} = C_{NDC} - C_{Bliss} = 0.5229 - 0.3782 = 0.1447$$

Bliss value of NDC (0.1447) is greater than zero, indicating that the two drugs in the NDC are synergistic in exhibiting anti-inflammatory effect.

NO Assay

After incubation, NO levels were quantified from half of the cell media using a Griess reagent assay kit (Promega, G2930). Colorimetric changes in the media and Griess reagent mixture were measured using a Synergy HTX Multi-Mode reader (Biotek) at 540 nm. All data were analyzed using the GraphPad Prism 9 software. Statistical significance was assessed using a one-way ANOVA or two-way ANOVA followed by Dunnett's post-hoc analysis unless otherwise noted. All data are presented as the mean±SEM, and significance was set at P<0.05. As can be seen from FIG. 5A and FIG. 5B, the combination of donepezil HCl and NAC (NDC) significantly reduced the content of NO in cells when compared with cells treated with donepezil HCl alone or NAC alone. (*P<0.05, P<0.01, *P<0.001, ****P<0.0001, one-way ANOVA). Additionally, the below Bliss Independence calculations show that the combination of NAC (antioxidant) and donepezil HCl (cholinesterase inhibitor) exhibits a synergistic effect in reducing the content of NO. The actual effect of NDC ($C_{NDC}$) in reducing the NO concentration is greater than the predicted response ($C_{Bliss}$) calculated using Bliss Independence model.

Figure 5A:
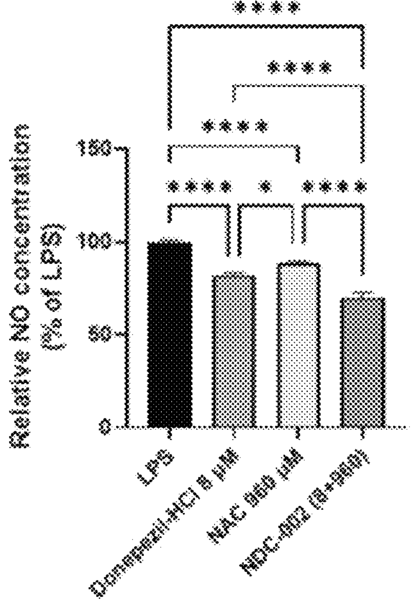
FIG. 5A illustrates the anti-inflammatory effect by measuring the concentration of nitric oxide (NO) generated in microglia cells treated with LPS, after treatment with donepezil (8 μM) alone, N-acetylcysteine (960 μM) alone or a combination of donepezil (8 μM) and N-acetylcysteine (960 μM).

Mean values from graph shown in FIG. 5A: LPS (100%), Donepezil-HCl (82.12%), NAC (88.44%), NDC (70.07%)

$$C_{Done}: LPS - \text{DONE} = 100(\%) - 82.12(\%) = 17.88(\%) = 0.1788$$

$$C_{NAC}: CTL - NAC = 100(\%) - 88.44(\%) = 11.56(\%) = 0.1156$$

$$C_{Bliss} = C_{Done} + C_{NAC} - C_{Done} * C_{NAC} = 0.1788 + 0.1156 - (0.1788 * 0.1156) = 0.2737$$

$$\text{Predicted response} = C_{Bliss} * 100 = 0.2737 * 100 = 27.37(\%)$$

$$C_{NDC}: LPS - NDC = 100(\%) - 70.07(\%) = 29.93(\%) = 0.2993$$

$$\text{Bliss value} = C_{NDC} - C_{Bliss} = 0.2993 - 0.2737 = 0.0256$$

Bliss value of NDC (0.0256) is greater than zero, indicating that the two drugs in the NDC are synergistic in exhibiting anti-inflammatory effect.

Figure 5B:
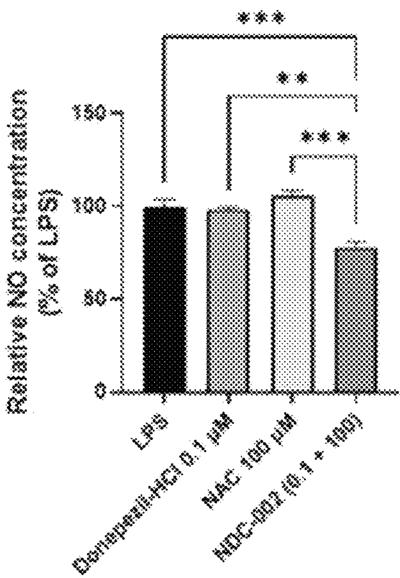
FIG. 5B illustrates the anti-inflammatory effect by measuring the concentration of nitric oxide (NO) generated in microglia cells treated with LPS, after treatment with donepezil (0.1 μM) alone, N-acetylcysteine (100 μM) alone or a combination of donepezil (0.1 μM) and N-acetylcysteine (100 μM).

Mean values from graph shown in FIG. 5B: LPS (100%), Donepezil-HCl (98.33%), NAC (105.68%), NDC (77.80%)

$$C_{Done}: LPS - \text{DONE} = 100(\%) - 98.33(\%) = 1.67(\%) = 0.0167$$

$$C_{NAC}: LPS - NAC = 100(\%) - 105.68(\%) = -5.68(\%) = -0.0568$$

$$C_{Bliss} = C_{Done} + C_{NAC} - C_{Done} * C_{NAC} = 0.0167 + (-0.0568) - (0.0167 * (-0.0568)) = -0.0391$$

$$\text{Predicted response} = C_{Bliss} * 100 = (-0.0391) * 100 = -3.91(\%)$$

$$C_{NDC}: LPS - NDC = 100(\%) - 77.80(\%) = 22.20\ (\%) = 0.222$$

$$\text{Bliss value} = C_{NDC} - C_{Bliss} = 0.222 - (-0.0391) = 0.2611$$

Bliss value of NDC (0.2611) is greater than zero indicating that the two drugs in the NDC are synergistic in exhibiting anti-inflammatory effect.

Figure 6:
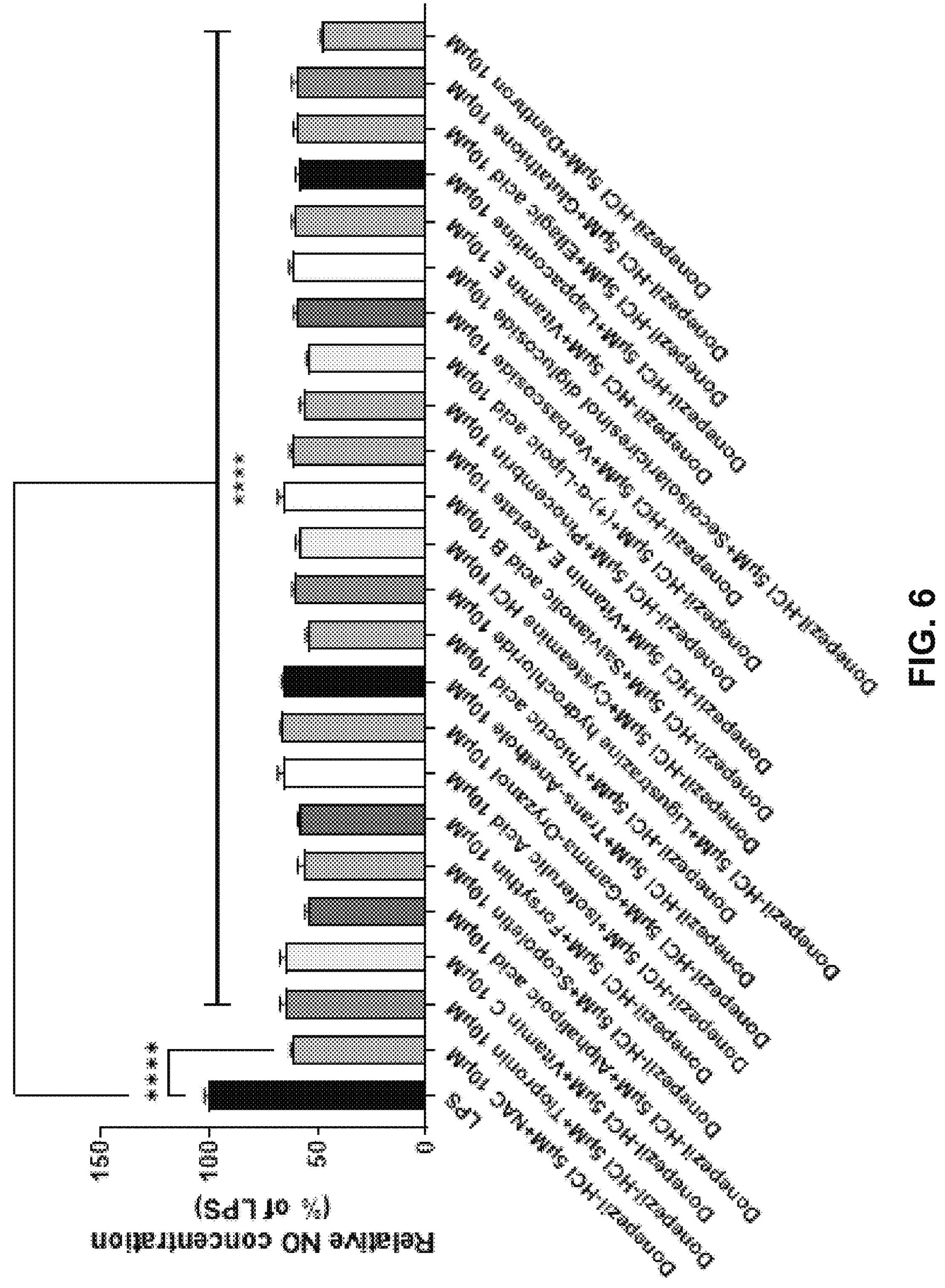
FIG. 6 illustrates the anti-inflammatory effect of combinations of donepezil and different antioxidants by measuring the amount of NO generated in microglia cells treated with LPS.

As seen in FIG. 6, combinations of donepezil HCl and antioxidant drugs other than NAC also significantly reduced the content of NO in LPS treated cells when compared to no treatment, indicating the anti-inflammatory effect of such combinations. (****P<0.0001, one-way ANOVA).

Figure 7:
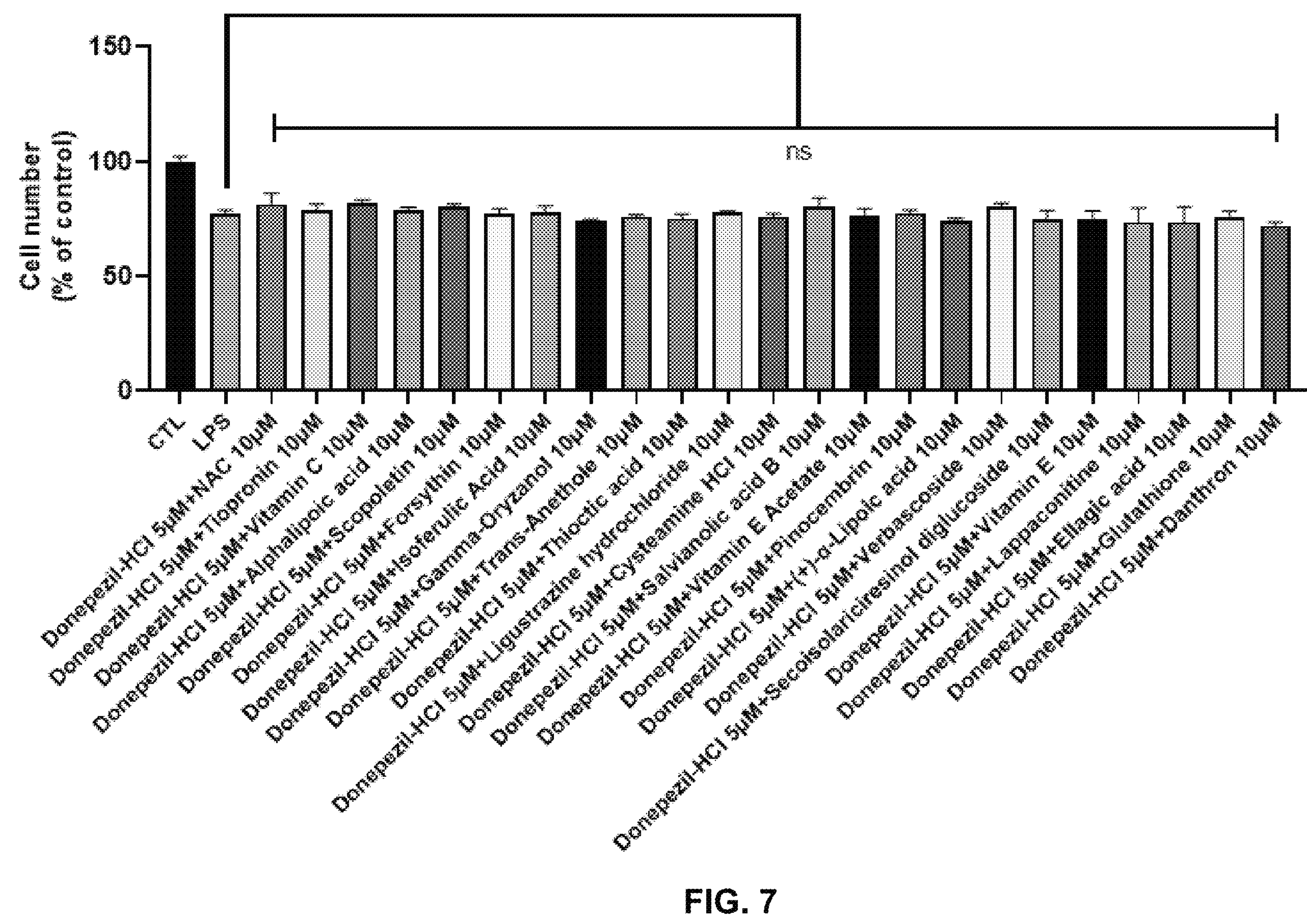
FIG. 7 illustrates the cytotoxicity of combinations of donepezil and different antioxidants in microglia cells treated with LPS by measuring the number of viable cells in the media.

As seen in FIG. 7, the number of viable cells (cytotoxicity) present in a media after treatment of microglia cells treated with LPS with combinations of donepezil HCl and various antioxidant drugs. As seen from the graph, that there was no significant difference in the number of viable cells in LPS treated microglial cells as compared to such cells further treated with the combination of donepezil HCl and an antioxidant indicating that the combinations of donepezil HCl and antioxidant tested were not cytotoxic.

Figure 8:
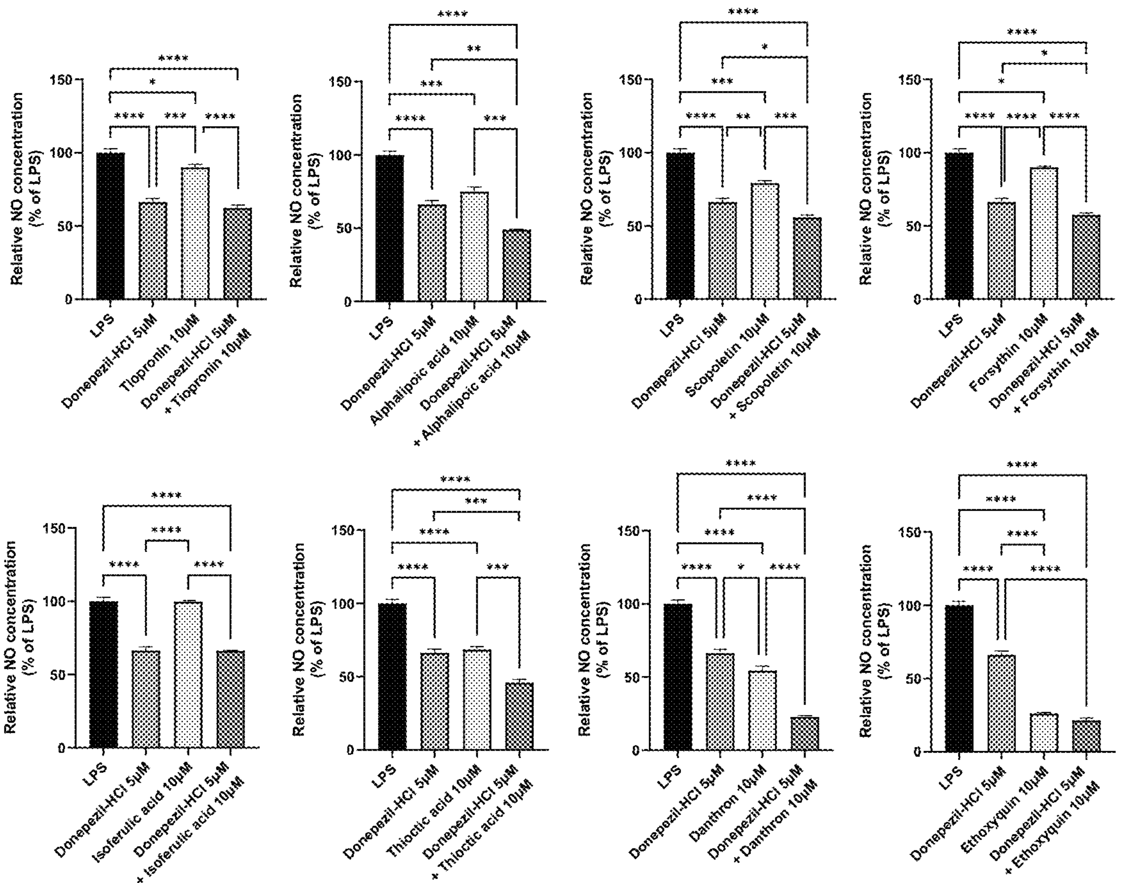
FIG. 8 illustrates the anti-inflammatory effect by measuring the concentration of NO generated in microglia cells treated with LPS, after treatment with donepezil alone, an antioxidant alone or a combination of donepezil and an antioxidant.

As seen in FIG. 8, the combination of donepezil HCl with an antioxidant drug other than NAC also significantly reduces the content of NO in LPS treated cells, when compared with NO levels in LPS treated cells treated with donepezil HCl alone or the antioxidant alone. (*P<0.05, P<0.01, *P<0.001, ****P<0.0001, one-way ANOVA). Additionally, the below Bliss Independence calculations show that certain combinations of donepezil HCl and an antioxidant other than NAC (referred to in below calculations as "Combination" or "Combi") also exhibit a synergistic effect in reduction of NO in LPS treated cells. For such combinations, the actual effect of the drug combination ($C_{Combi}$) in reducing the NO concentration is greater than the predicted response ($C_{Bliss}$) calculated using Bliss independence model.

BLISS calculations for Tiopronin. Mean values from graph shown in FIG. 8 for Tiopronin (referred to herein as "Tio"): LPS (100%), Donepezil-HCl (66.26%), Tiopronin (89.97%), Combination (62.25%)

$$C_{Done}: LPS - \text{DONE} = 100(\%) - 66.26(\%) = 33.74(\%) = 0.3374$$

$$C_{Tio}: LPS - Tio = 100(\%) - 89.97(\%) = 10.03(\%) = 0.1003$$

$$C_{Bliss} = C_{Done} + C_{Tio} - C_{Done} * C_{Tio} = 0.3374 + 0.1003 - (0.3374 * 0.1003) = 0.4039$$

$$\text{Predicted response} = C_{Bliss} * 100 = 0.4039 * 100 = 40.39(\%)$$

$$C_{Combi}: LPS - Combi = 100(\%) - 62.25(\%) = 37.75\ (\%) = 0.3775$$

-continued $$\text{Bliss value} = C_{Combi} - C_{Bliss} = 0.3775 - 0.4039 = -0.0264$$

Bliss value of Combi (−0.0264) is less than zero, indicating that the two drugs in this Combination (Donepezil HCl and Tiopronin) were not synergistic in exhibiting anti-inflammatory effect.

Bliss calculations for Alphalipoic acid. Mean values from graph shown in FIG. 8 for Alphalipoic acid (referred to herein as "Alp"): LPS (100%), Donepezil-HCl (66.26%), Alphalipoic acid (75.02%), Combination (48.94%)

$$C_{Done}: LPS - \text{DONE} = 100(\%) - 66.26(\%) = 33.74(\%) = 0.3374$$

$$C_{Alp}: LPS - Alp = 100(\%) - 75.02(\%) = 24.98(\%) = 0.2498$$

$$C_{Bliss} = C_{Done} + C_{Alp} - C_{Done} * C_{Alp} = 0.3374 + 0.2498 - (0.3374 * 0.2498) = 0.5029$$

$$\text{Predicted response} = C_{Bliss} * 100 = 0.5029 * 100 = 50.29(\%)$$

$$C_{Combi}: LPS - Combi = 100(\%) - 48.94(\%) = 51.06(\%) = 0.5106$$

$$\text{Bliss value} = C_{Combi} - C_{Bliss} = 0.5106 - 0.5029 = 0.0077$$

Bliss value of Combi (0.0077) is greater than zero, indicating that the two drugs in this combination (Donepezil HCl and Alphalipoic acid) are synergistic in exhibiting anti-inflammatory effect.

Bliss calculations for Scopoletin. Mean values from graph shown in FIG. 8 for Scopoletin (referred to herein as "Sco"): LPS (100%), Donepezil-HCl (66.26%), Scopoletin (79.21%), Combination (55.69%)

$$C_{Done}: LPS - \text{DONE} = 100(\%) - 66.26(\%) = 33.74(\%) = 0.3374$$

$$C_{Sco}: LPS - Sco = 100(\%) - 79.21(\%) = 20.79(\%) = 0.2079$$

$$C_{Bliss} = C_{Done} + C_{Sco} - C_{Done} * C_{Sco} = 0.3374 + 0.2079 - (0.3374 * 0.2079) = 0.4751$$

$$\text{Predicted response} = C_{Bliss} * 100 = 0.4751 * 100 = 47.51(\%)$$

$$C_{Combi} := LPS - Combi = 100(\%) - 55.69(\%) = 44.31\ (\%) = 0.4431$$

$$\text{Bliss value} = C_{Combi} - C_{Bliss} = 0.4431 - 0.4751 = -0.0320$$

Bliss value of Combi (−0.0320) is less than zero, indicating that the two drugs in this Combination (Donepezil HCl and Scopoletin) were not synergistic in exhibiting anti-inflammatory effect.

Bliss calculations for Forsythin. Mean values from graph shown in FIG. 8 for Forsythin (referred to herein as "For"): LPS (100%), Donepezil-HCl (66.26%), Forsythin (89.97%), Combination (57.51%)

$$C_{Done}: LPS - \text{DONE} = 100(\%) - 66.26(\%) = 33.74(\%) = 0.3374$$

$$C_{For}: LPS - \text{For} = 100(\%) - 89.97(\%) = 10.03(\%)10.03 = 0.1003$$

$$C_{Bliss} = C_{Done} + C_{For} - C_{Done} * C_{For} = 0.3374 + 0.1003 - (0.3374 * 0.1003) = 0.4039$$

$$\text{Predicted response} = C_{Bliss} * 100 = 0.4039 * 100 = 40.39(\%)$$

-continued $$C_{Combi}: LPS - Combi = 100(\%) - 57.51(\%) = 42.49(\%) = 0.4249$$

$$\text{Bliss value} = C_{Combi} - C_{Bliss} = 0.4249 - 0.4039 = 0.0210$$

Bliss value of Combi (0.0210) is greater than zero, indicating that the two drugs in this combination (Donepezil HCl and Forsythin) are synergistic in exhibiting anti-inflammatory effect.

Bliss calculations for Isoferulic acid. Mean values from graph shown in FIG. 8 for Isoferulic acid (referred to herein as "Iso"): LPS (100%), Donepezil-HCl (66.26%), Isoferulic acid (99.64%), Combination (66.08%)

$$C_{Done}: LPS - \text{DONE} = 100(\%) - 66.26(\%) = 33.74(\%) = 0.3374$$

$$C_{Iso}: LPS - Iso = 100(\%) - 99.64(\%) = 0.36(\%)$$

$$C_{Bliss} = C_{Done} + C_{Iso} - C_{Done} * C_{Iso} = 0.3374 + 0.0036 - (0.3374 * 0.0036) = 0.3398$$

$$\text{Predicted response} = C_{Bliss} * 100 = 0.3398 * 100 = 33.98(\%)$$

$$C_{Combi}: LPS - Combi = 100(\%) - 66.08(\%) = 33.92\ (\%) = 0.3392$$

$$\text{Bliss value} = C_{Combi} - C_{Bliss} = 0.3392 - 0.3398 = -0.0006$$

Bliss value of Combi (−0.0006) is less than zero, indicating that the two drugs in this Combination (Donepezil HCl and Isoferulic acid) were not synergistic in exhibiting anti-inflammatory effect.

Bliss calculations for Thioctic acid. Mean values from graph shown in FIG. 8 for Thioctic acid (referred to herein as "Thi"): LPS (100%), Donepezil-HCl (66.26%), Thioctic acid (68.45%), Combination (45.84%)

$$C_{Done}: LPS - \text{DONE} = 100(\%) - 66.26(\%) = 33.74(\%) = 0.3374$$

$$C_{Thi}: LPS - Thi = 100(\%) - 68.45(\%) = 31.55(\%) = 0.3155$$

$$C_{Bliss} = C_{Done} + C_{Thi} - C_{Done} * C_{Thi} = 0.3374 + 0.3155 - (0.3374 * 0.3155) = 0.5464$$

$$\text{Predicted response} = C_{Bliss} * 100 = 0.5464 * 100 = 54.64(\%)$$

$$C_{Combi}: CTL - Combi = 100(\%) - 45.84(\%) = 54.16\ (\%)$$

$$\text{Bliss value} = C_{Combi} - C_{Bliss} = 0.5416 - 0.5464 = -0.0048$$

Bliss value of Combi (−0.0048) is less than zero, indicating that the two drugs in this Combination (Donepezil HCl and Thioactic acid) were not synergistic in exhibiting anti-inflammatory effect.

Bliss calculations for Danthron. Mean values from graph shown in FIG. 8 for Danthron (referred to herein as "Dan"): LPS (100%), Donepezil-HCl (66.26%), Dan (54.23%), Combination (22.68%)

$$C_{Done}: LPS - \text{DONE} = 100(\%) - 66.26(\%) = 33.74(\%) = 0.3374$$

$$C_{Dan}: LPS - Dan = 100(\%) - 54.23(\%) = 45.77(\%) = 0.4577$$

$$C_{Bliss} = C_{Done} + C_{DaI} - C_{Done} * C_{Dan} = 0.3374 + 0.4577 - (0.3374 * 0.4577) = 0.6407$$

-continued $$\text{Predicted response} = C_{Bliss} * 100 = 0.6407 * 100 = 64.07(\%)$$

$$C_{Combi}: LPS - Combi = 100(\%) - 22.68(\%) = 77.32(\%) = 0.7732$$

$$\text{Bliss value} = C_{Combi} - C_{Bliss} = 0.7732 - 0.6407 = 0.1325$$

Bliss value of Combi (0.1325) is greater than zero, indicating that the two drugs in this combination (Donepezil HCl and Danthron) are synergistic in exhibiting anti-inflammatory effect.

Bliss calculations for Ethoxyquin. Mean values from graph shown in FIG. 8 for Ethoxyquin: LPS (100%), Donepezil-HCl (66.26%), Ethoxyquin (26.15%), Combination (21.41%)

$$C_{Done}: LPS - \text{DONE} = 100(\%) - 66.26(\%) = 33.74(\%) = 0.3374$$

$$E_{Eth}: LPS - Eth = 100(\%) - 26.15(\%) = 73.85(\%) = 0.7385$$

$$C_{Bliss} =$$

$$C_{Done} + C_{Eth} - C_{Done} * C_{Eth} = 0.3374 + 0.7385 - (0.3374 * 0.7385) = 0.8267$$

$$\text{Predicted response} = C_{Bliss} * 100 = 0.8267 * 100 = 82.67(\%)$$

$$C_{Combi} = CTL - Combi = 100(\%) - 21.41(\%) = 78.59\ (\%) = 0.7859$$

$$\text{Bliss value} = C_{Combi} - C_{Bliss} = 0.7859 - 0.8267 = -0.0408$$

Bliss value of Combi (−0.0408) is less than zero, indicating that the two drugs in this Combination (Donepezil HCl and Ethoxyquin) were not synergistic in exhibiting anti-inflammatory effect.

Example 4

Promotion of Neural Progenitor Cell Differentiation by Combination of Cholinesterase Inhibitor and Antioxidant ReN VM-immortalized cells, human neural progenitor cell line, were used (EMD Millipore, SCC008). These neural progenitor cells can differentiate into motor neurons and glial cells. The degree of differentiation of neural progenitor cells into motor neurons was determined by analysing the level of HB9, a specific motor neuron marker. ReN VM cells were cultured on laminin (Corning, 354232)-coated 75T Flask in the growth medium, which is DMEM/F12 (Welgene, #LM002-08) supplemented with 20 ng/ml basic fibroblast growth factor (bFGF; Gibco, 15750-060), 20 ng/ml epidermal growth factor (EGF; Sigma, E9644), serum-free B27 (Gibco, 17504-044), 10 KU heparin (Sigma, H3393), and 1% gentamicin (Gibco, 17504-044). Cells were plated in 96-well plates at 7000 cells/well in the growth media in a 37° C./5% CO2 incubator for 3 days. Subsequently, the growth medium was replaced with a differentiation medium (growth medium without bFGF and EGF), and the cells were treated with the drugs (donepezil HCl alone, NAC alone, and donepezil HCl+NAC) for 3 days. Immunostaining was performed against HB9, a specific motor neuronal marker, to assess the population of motor neurons. Briefly, drug-treated ReN VM cells were fixed in 10% formalin solution for 20 minutes and permeabilized in 0.1% TritonX-100. After incubation with Intercept® Blocking buffer (LI-COR, 927, 60001) for 1 hour, the cells were incubated with rabbit anti-HB9 antibody (1:300, Abcam, ab97541) overnight at 4° C. After washing with 0.1% TritonX-100 solution, cells were incubated for 1 hour with IRDye® 800 CW goat anti-rabbit IgG (1:1000, LI-COR, 925-32211) and CellTag700 (1:1000, LI-COR, 926-41090) for normalization of cell number. Fluorescence intensity levels were measured using an Odyssey® DLx Infrared Imaging System (LI-COR, CLS-2383). All data were analyzed using the GraphPad Prism 9 software. Statistical significance was assessed using a one-way ANOVA or two-way ANOVA followed by Dunnett's post-hoc analysis unless otherwise noted. All data are presented as the mean±SEM, and significance was set at P<0.05.

Figure 9A:
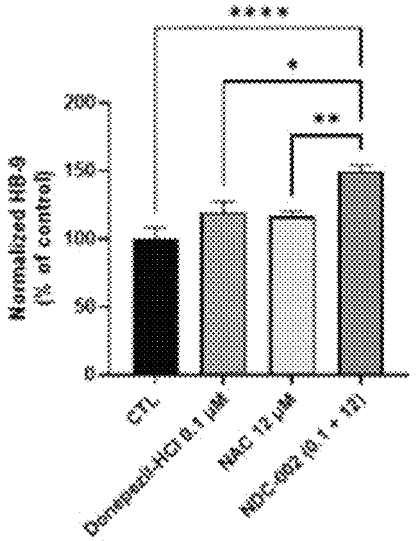
FIG. 9A illustrates the expression level of HB9, a motor neuron marker, after treatment of neural progenitor cells with donepezil (0.1 μM) alone, N-acetylcysteine (12 μM) alone or a combination of donepezil (0.1 μM) and N-acetylcysteine (12 μM).
Figure 9B:
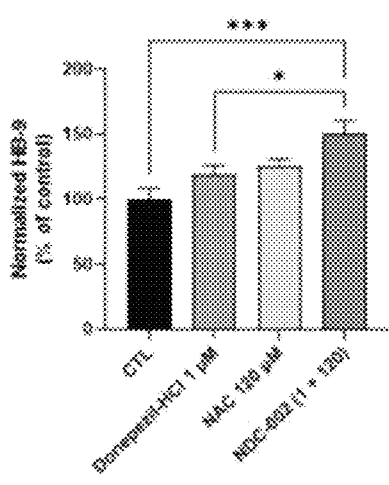
FIG. 9B illustrates the expression level of HB9, a motor neuron marker, after treatment of neural progenitor cells with donepezil (1 μM) alone, N-acetylcysteine (120 μM) alone or a combination of donepezil (1 μM) and N-acetylcysteine (120 μM).

As can be seen from FIG. 9A and FIG. 9B, the expression level of HB9, a motor neuron marker, was significantly increased after treatment with combination of donepezil HCl and NAC when compared with cells treated with donepezil HCl alone or NAC alone. (*P<0.05, P<0.01, *P<0.001, ****P<0.0001, one-way ANOVA). Additionally, the below Bliss Independence calculations show that the combination of NAC and donepezil HCl exhibits a synergistic effect in increasing the HB9 levels, and, hence, the motor neuron activity. The actual effect of NDC ($C_{NDC}$) in increasing the HB9 levels is greater than the predicted response ($C_{Bliss}$) calculated using Bliss Independence model.

Mean value from graph shown in FIG. 9A: CTL (100%), Donepezil-HCl (119.81%), NAC (116.9%), NDC (150.1%)

$$C_{Done}: \text{DONE} - CTL = 119.81(\%) - 100(\%) = 19.81(\%) = 0.1981$$

$$C_{NAC}: NAC - CTL = 116.9(\%) - 100(\%) = 16.9(\%)$$

$$C_{Bliss} =$$

$$C_{Done} + C_{NAC} - C_{done} * C_{NAC} = 0.1981 + 0.169 - (0.1981 * 0.169) = 0.3336$$

$$\text{Predicted response} = C_{Bliss} * 100 = 0.3336 * 100 = 33.36(\%)$$

$$C_{NDC}: NDC - CTL = 150.1(\%) - 100(\%) = 50.1(\%) = 0.501$$

$$\text{Bliss value} = C_{NDC} - C_{Bliss} = 0.501 - 0.3336 = 0.1674$$

Bliss value of NDC (0.1674) is greater than zero indicating that the two drugs in the NDC are synergistic in promoting neural progenitor cells differentiation into motor neurons.

Mean value from graph shown in FIG. 9B: CTL (100%), Donepezil-HCl (119.25%), NAC (125.36%), NDC (150.83%)

$$C_{Done}: \text{DONE} - CTL = 119.25(\%) - 100(\%) = 19.25(\%) = 0.1925$$

$$C_{NAC}: NAC - CTL = 125.36(\%) - 100(\%) = 25.36(\%) = 0.2536$$

$$C_{Bliss} = C_{Done} + C_{NAC} - C_{Done} * C_{NAC} =$$

$$0.1925 + 0.2536 - (0.1925 * 0.2536) = 0.3973$$

$$\text{Predicted response} = C_{Bliss} * 100 = 0.3973 * 100 = 39.73$$

$$C_{NDC}: NDC - CTL = 150.83(\%) - 100(\%) = 50.83(\%) = 0.5083$$

$$\text{Bliss value} = C_{NDC} - C_{Bliss} = 0.5083 - 0.3973 = 0.111$$

Bliss value of NDC (0.111) is greater than zero indicating that the two drugs in the NDC are synergistic in promoting neural progenitor cells differentiation into motor neurons.

Figure 10A:
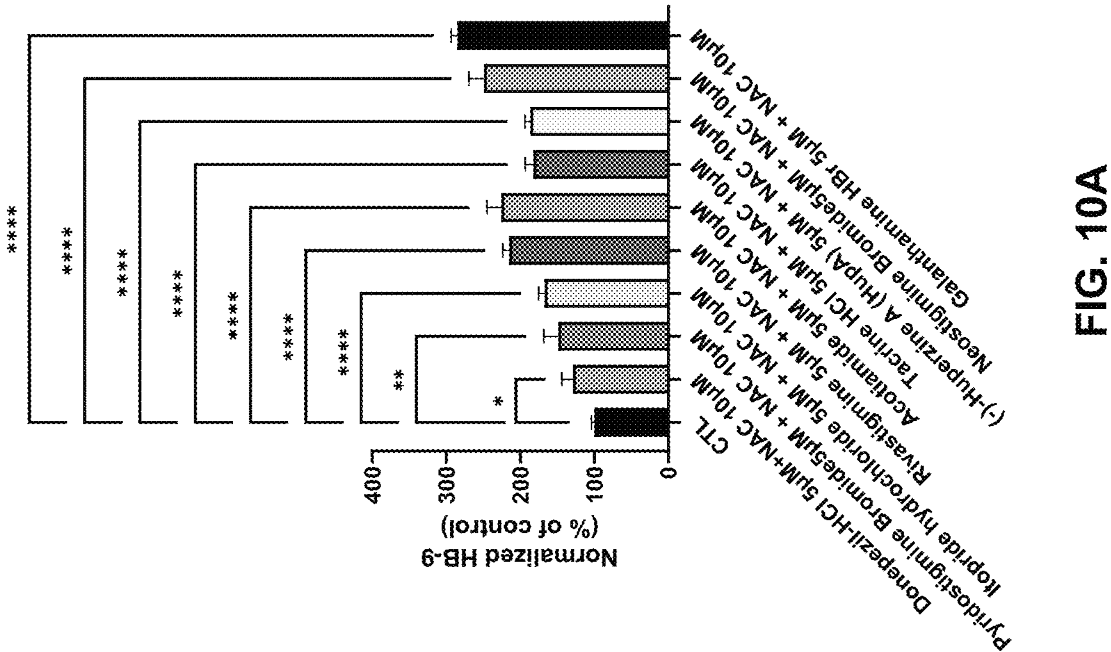
FIG. 10A illustrates the expression level of HB9, a motor neuron marker, after treatment of neural progenitor cells with combinations of N-acetylcysteine and different cholinesterase inhibitors.

As seen in FIG. 10A, combinations of NAC and cholinesterase inhibitors other than donepezil HCl also significantly increased the expression level of HB9, a motor neuron marker, after treatment of neural progenitor cells with such combinations when compared to no treatment, indicating that combinations of NAC and cholinesterase inhibitors promote differentiation of neural progenitor cells into the motor neurons. (*P<0.05, P<0.01, *P<0.001, ****P<0.0001, unpaired t-test).

Figure 10B:
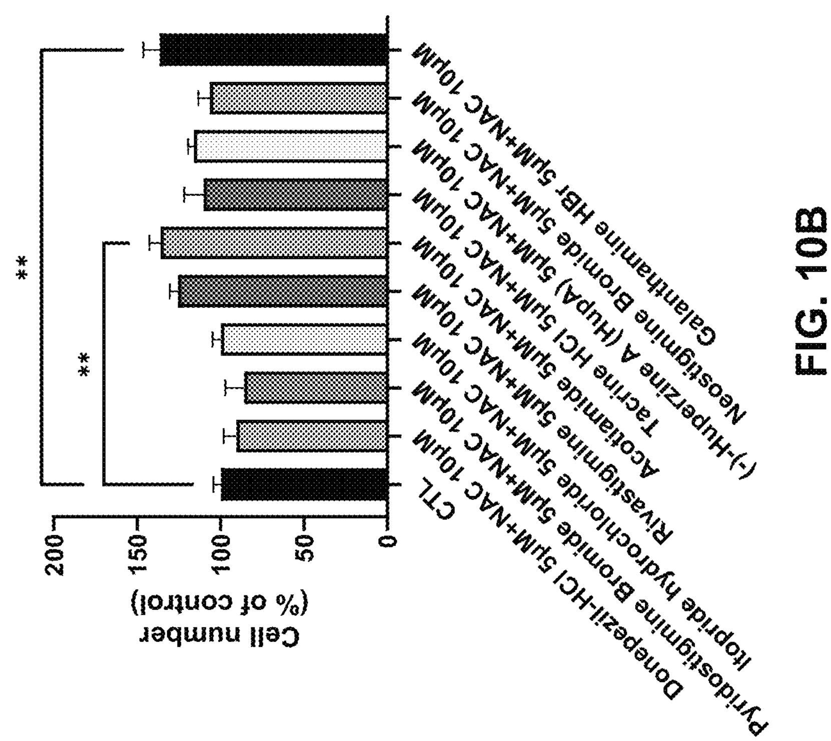
FIG. 10B illustrates the cytotoxicity of combinations of N-acetylcysteine and different cholinesterase inhibitors in neural progenitor cells by measuring the number of viable cells present in the media.

As seen in FIG. 10B, the number of living cells (cytotoxicity) present in a media treated with the combination of NAC and different cholinesterase inhibitors show no or negligible cytotoxicity when compared with the control group (*P<0.05, P<0.01, *P<0.001, ****P<0.0001, unpaired t-test).

Figure 11:
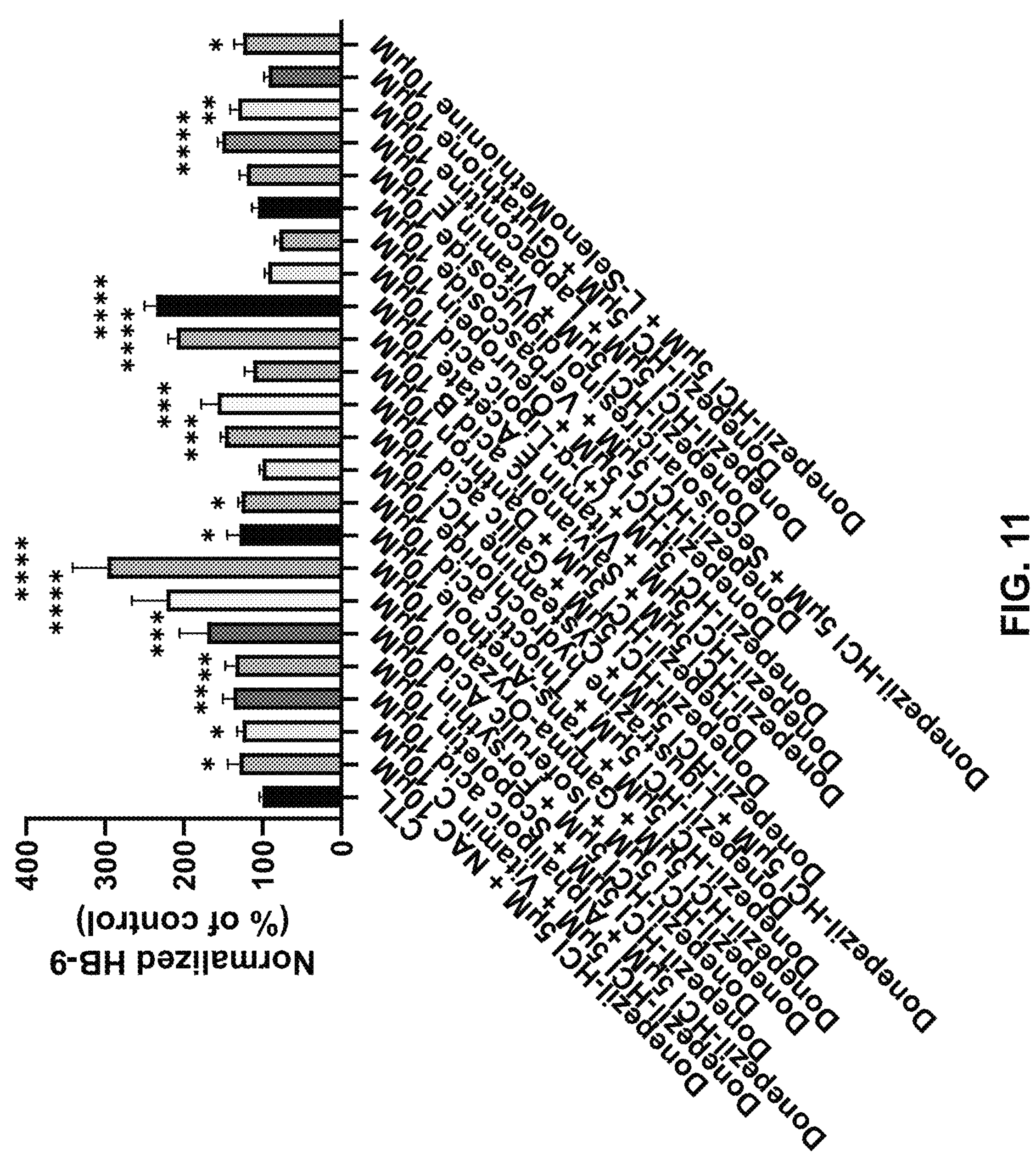
FIG. 11 illustrates the expression level of HB9, a motor neuron marker, after treatment of neural progenitor cells with combinations of donepezil and different antioxidants.

As seen in FIG. 11, combinations of donepezil HCl and antioxidants other than NAC also significantly increased the expression level of HB9, a motor neuron marker, after treatment of neural progenitor cells with such combinations as compared to no treatment, indicating that certain combinations of donepezil HCl and antioxidants promote differentiation of neural progenitor cells into the motor neurons. (*P<0.05, P<0.01, *P<0.001, ****P<0.0001, unpaired t-test).

Figure 12:
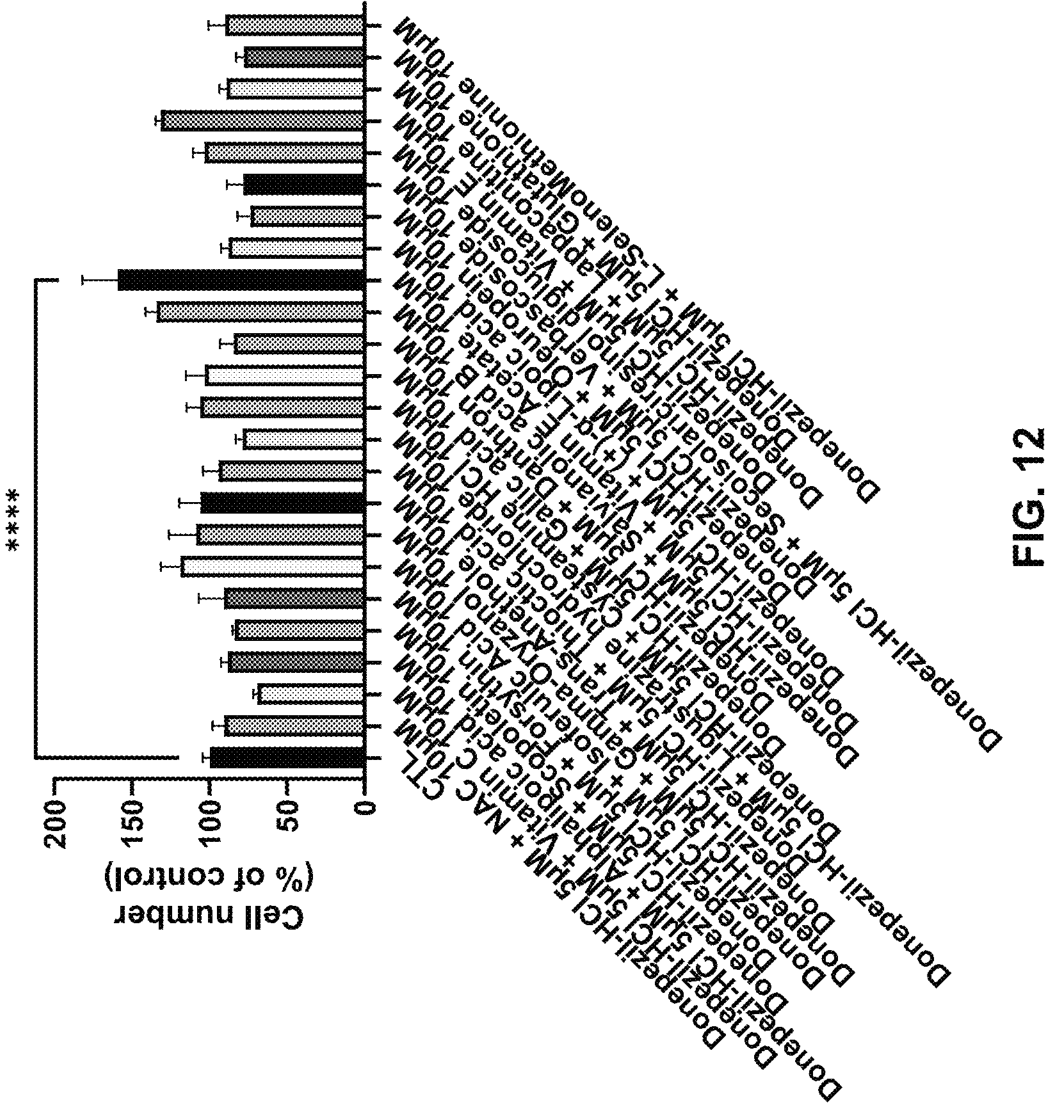
FIG. 12 illustrates the cytotoxicity of combinations of donepezil and different antioxidants in neural progenitor cells by measuring the number of viable cells.

As seen in FIG. 12, the number of living cells (cytotoxicity) present in a media treated with the combination of donepezil HCl and different antioxidants show no or negligible cytotoxicity when compared with the control group (no treatment). (*P<0.05, P<0.01, *P<0.001, ****P<0.0001, unpaired t-test).

Figures 13A, 13B:
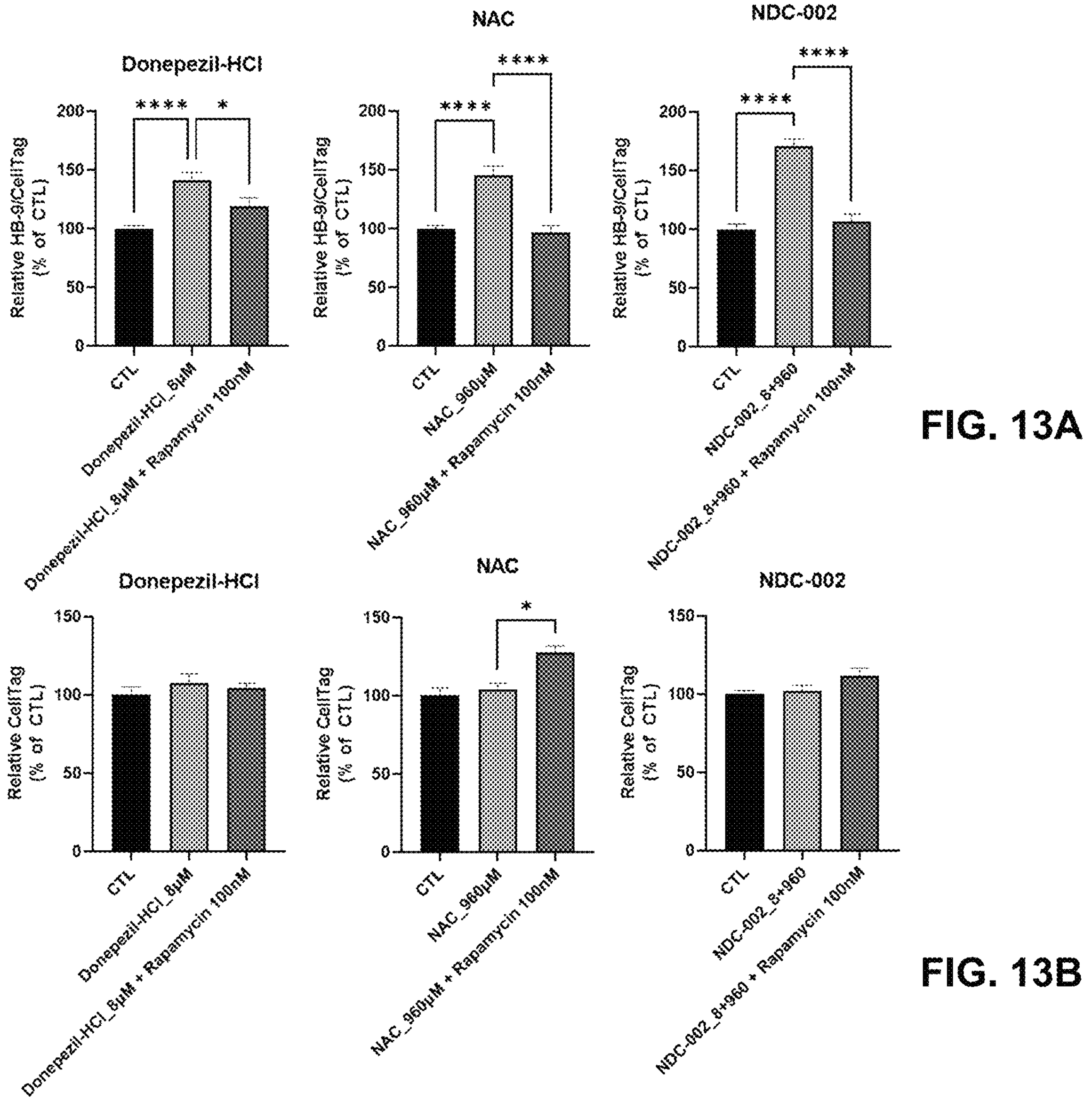
FIG. 13A illustrates the involvement of mTOR pathway in the differentiation of neural progenitor cells treated with donepezil alone, N-acetylcysteine alone and combination of donepezil and N-acetylcysteine.
FIG. 13B illustrates the cytotoxicity of donepezil alone, N-acetylcysteine alone and combination of donepezil and N-acetylcysteine in the presence and absence of rapamycin by measuring the number of viable cells.

As seen in FIG. 13A, the levels of HB9, a motor neuron marker, significantly decreased when rapamycin (a known pharmacological inhibitor of the mTOR pathway) was added to cells treated with NDC-002 as compared to the levels of HB9 in the presence of NDC-002 alone. Further, as seen in FIG. 13B, the addition of rapamycin did not induce cytotoxicity. These results indicate that the differentiation of neural progenitor cells into motor neurons by the combination of donepezil HCl and NAC involves mTOR pathway.

Example 5

Enhancement of Synaptic Plasticity by Combination of Cholinesterase Inhibitor and Antioxidant (In-Vitro Study)

Type-specific biomarkers exist to identify cognitive and memory-enhancing functions. These include neuroprotective effects through inhibition of neuronal cell death, inhibition of beta amyloid formation and accumulation, inhibition of neuroinflammation, modulation of neurotransmitter production, secretion, and metabolism, and modulation of synaptic plasticity.

Regulation of synaptic plasticity is an important type of cognitive effect through its involvement in signaling between neurons, and its biomarkers include postsynaptic density-95 (PSD-95), CREB and BGNF.

Postsynaptic density-95 (PSD-95) is an essential family of functional molecules that are part of the postsynaptic density (PSD) and play an essential role in the induction of long-term potentiation (LTP), including NMDA receptors and CaMKII. By binding directly or indirectly to neuroligins, NMDA receptors, AMPA receptors, and potassium channels, they play an important role in synaptic plasticity and the safety of synaptic changes during LTP (Ehrlich et al., PSD-95 is required for activity-driven synapse stabilization, PNAS 2007./Nagura et al., Impaired synaptic clustering of postsynaptic density proteins and altered signal transmission in hippocampal neurons, and disrupted learning behavior in PDZ1 and PDZ2 ligand binding deficient PSD-95 knockin mice, Molecular Brain, 2012.).

On the other hand, cAMP response element-binding protein (CREB) is a transcription factor that binds to promoter sites of various genes involved in memory and synaptic plasticity, and activation of CREB is known to induce transcription of genes involved in memory formation and consolidation (such as BDNF) (Mizuno et al., CREB phosphorylation as a molecular marker of memory processing in the hippocampus for spatial learning. Behavioral Brain Research, 2002./Kida et al., Functional roles of CREB as a positive regulator in the formation and enhanced of memory, Brain Research Bulletin, 2014).

To evaluate the synaptic plasticity, primary neuro-glia culture was prepared from cortices of embryonic day 16 C57/BL6 mice. Cells were collected by mechanical dissection and chemical dissociation with trypsin and DNase treatment and cultured in Neurobasal (NB) and MEM media supplemented with 1% B-27, 2 mM L-glutamine, 5% Fetal Bovine Serum, 5% Horse Serum, 1×MEM-NEAA (non-essential amino acids), and 1% Penicillin-Streptomycin (PS). Cells were cultured in Poly-D-Lysine+Laminin-coated 6-well plates at 2×106 cells/well in growth media. After 3 days in vitro (DIV 3), media was changed to NB media supplemented with 2% B-27, 2 mM L-glutamine, and 1% PS. At DIV 6, cells were treated with donepezil HCl+NAC (NDC), donepezil HCl (DONE) alone, and NAC alone for 4 days and protein extraction was carried out with RIPA. Protein was resolved by 8% SDS-PAGE electrophoresis, transferred to polyvinylidene difluoride membranes and blocked with 5% non-fat dry milk for 1 hour at RT. Membrane was immunoblotted using following antibodies; primary antibody: PSD-95 (Abcam, ab18258, 1:2,000), phospho-CREB (Millipore, #06-519, 1:2,000), β-actin (Cell signaling, #3700, 1:3,000), and secondary antibody:HRP-conjugated anti-mouse IgG (AbFrontier, LF-SA8001, 1:5,000), HRP-conjugated anti-rabbit IgG (AbFrontier, LF-SA8002, 1:5,000). Signal was visualized by chemiluminescence methods using ECL solution and imaged using ImageQuant LAS 500 system. PSD-95 and phosphor-CREB band intensity was divided by β-actin band intensity for corresponding lane and data was normalized to mean value of untreated control group for presentation. Total number of wells per group was 6 (n=6).

Figure 14A:
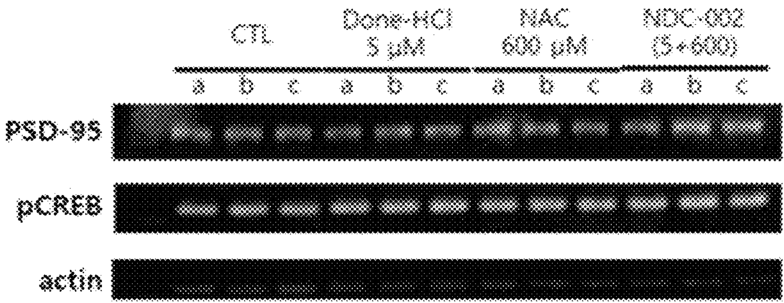
FIG. 14A illustrates PSD-95, pCREB and actin protein bands as resolved by SDS-PAGE electrophoresis, wherein protein was extracted from primary cultured neurons from mouse fetal brains after treatment with donepezil alone, N-acetylcysteine alone, or a combination of donepezil and N-acetylcysteine.
Figure 14B:
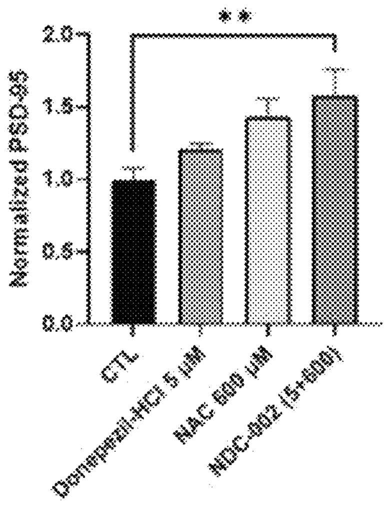
FIG. 14B illustrates the difference in expression of PSD-95 involved in the regulation of synaptic plasticity in mouse-derived primary cultured neurons after treatment with donepezil alone, N-acetylcysteine alone, or a combination of donepezil and N-acetylcysteine.

As seen in FIG. 14B, the treatment with combination of donepezil HCl and NAC significantly increased the expression of PSD-95 when to the control (no treatment). (**P<0.01, one-way ANOVA). Additionally, the below Bliss Independence calculations show that the combination of donepezil HCl and NAC exhibits a synergistic effect in increasing PSD-95 expression and pCREB expression, and, hence, synaptic plasticity. The actual effect of NDC ($C_{NDC}$) on increase in the expression levels of these two markers is greater than the predicted response ($C_{Bliss}$) calculated using Bliss Independence model.

Mean value from graph shown in FIG. 14B: CTL (1.0), Donepezil-HCl (1.20), NAC (1.43), NDC (1.58)

$$C_{Done}\text{: DONE} - CTL = 1.20 - 1.0 = 0.2$$

$$C_{NAC}: NAC - CTL = 1.43 - 1.0 = 0.43$$

$$C_{Bliss} = C_{Done} + C_{NAC} - C_{Done} * C_{NAC} = 0.2 + 0.43 - (0.2 * 0.43) = 0.54$$

$$\text{Predicted response} = C_{Bliss} = 0.54$$

$$C_{NDC}: NDC - CTL = 1.58 - 1.0 = 0.58$$

-continued $$\text{Bliss value} = C_{NDC} - C_{Bliss} = 0.58 - 0.54 = 0.04$$

Bliss value of NDC (0.04) is greater than zero, indicating that the two drugs in the NDC are synergistic in increasing PSD-95 expression, and, hence, synaptic plasticity.

Figure 14C:
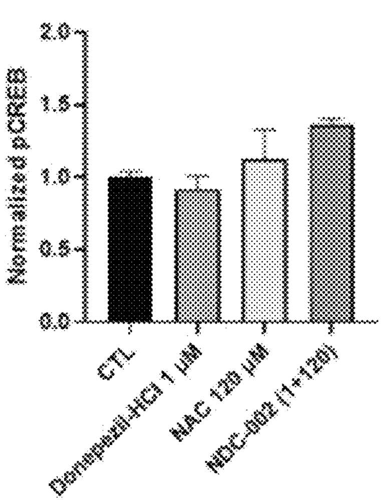
FIG. 14C illustrates the difference in expression of pCREB involved in the regulation of synaptic plasticity in mouse-derived primary cultured neurons after treatment with donepezil alone, N-acetylcysteine alone, or a combination of donepezil and N-acetylcysteine.

Mean value from graph shown in FIG. 14C: CTL (1.0), Donepezil-HCl (0.92), NAC (1.13), NDC (1.36)

$$C_{Done}: \text{DONE} - CTL = 0.92 - 1.0 = -0.08$$

$$C_{NAC}: NAC - CTL = 1.13 - 1.0 = 0.13$$

$$C_{Bliss} = C_{Done} + C_{NAC} - C_{Done} * C_{NAC} = (-0.08) + 0.13 - ((-0.08) * 0.13) = 0.06$$

$$\text{Predicted response} = C_{Bliss} = 0.06$$

$$C_{NDC}: NDC - CTL = 1.36 = 1.0 = 0.36$$

$$\text{Bliss value} = C_{NDC} - C_{Bliss} = 0.36 - 0.06 = 0.3$$

Bliss value of NDC (0.3) is greater than zero, indicating that the two drugs in the NDC are synergistic in increasing pCREB expression, and, hence, synaptic plasticity.

Example 6

Improvement in Motor Coordination and Extent of Brain Damage by Combination of Cholinesterase Inhibitor and Antioxidant (In-Vivo Study)

A stroke model was created using a cerebral infarction-reperfusion model in Sprague-Dawley rats (SD rats), and donepezil alone, NAC alone, and donepezil+NAC combination were administered I.V. for 21 days immediately after creating the cerebral infarction-reperfusion model.

The Rotarod test was performed on the 1, 3, 7, 14, and 21 days after 45 minutes-MCAO (middle cerebral artery occlusion)-reperfusion modelling to induced ischemia (Brain Stroke). The test was carried out 3 times per day and drugs (donepezil HCl+NAC (NDC), donepezil HCl alone and NAC alone) were administered 2 hours after MCAO induction for 21 days every day. The animal was carefully placed on a rotating rod (JD-A-07RA5, BS Technolab Inc., Korea) and the time (second) that animal was fallen was measured. The speed of rotating rod was increased from 4 rpm to 40 rpm for 300 second. The performance was compared between each group across all days of testing and the result was normalized by the fall latency of each group on day 1. For rotarod latency test, Nested one-way ANOVA and Two-way ANOVA was used to analyze significance between the groups on each day. Statistical analysis was performed using Prism 9 (GraphPad Software Inc., San Diego, CA, USA) and statistical significance was set at a P-value of less than 0.05.

Figure 15:
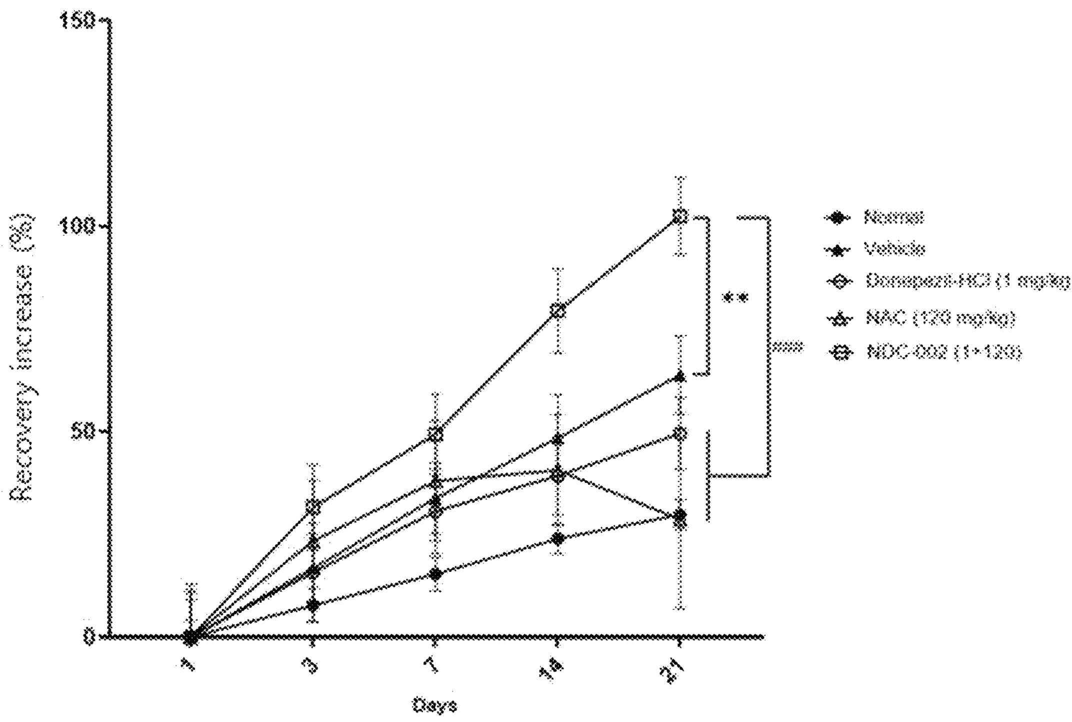
FIG. 15 illustrates the motor function recovery effect of treatment with donepezil alone, N-acetylcysteine alone, or a combination of donepezil and N-acetylcysteine using a stroke-reperfusion animal model.

As can be seen from FIG. 15, the motor co-ordination of the rats wherein MCAO was induced was found to be very poor with a low recovery rate in the absence of any treatment. However, treatment with the combination of donepezil HCl and NAC showed a significantly increased recovery rate (improved rotarod score), when compared to the recovery rate observed in rats treated with donepezil HCl alone or NAC alone. These results indicate a significant improvement in the motor coordination of rats suffering from ischemia upon treatment with the combination of donepezil HCl and NAC. (**P<0.01, and ###P<0.001, one-way ANOVA). Additionally, the below Bliss Independence calculations show that the combination of donepezil HCl and NAC exhibits a synergistic effect in improving motor coordination. The actual recovery rate of rats suffering from ischemia upon treatment with NDC ($C_{NDC}$) was greater than the predicted recovery rate ($C_{Bliss}$) calculated using Bliss Independence model.

Mean values from graph shown in FIG. 15 on day 3: VEH (16.69), DONE (15.77), NAC (23.39), NDC (31.60)
Normalized to VEH: VEH (100%), DONE (93.92%), NAC (139.30%), NDC (188.20%)

$$C_{Done}: \text{DONE} - VEH = 93.92(\%) - 100(\%) = -6.08(\%) = -0.0608$$

$$C_{NAC}: NAC - VEH = 139.30(\%) - 100(\%) = 39.30(\%) = 0.3930$$

$$C_{Bliss} = C_{Done} + C_{NAC} - C_{Done} * C_{NAC} = -0.0608 + 0.3930 - ((-0.1423) * (0.3930)) = 0.3561$$

$$\text{Predicted response} = C_{Bliss} * 100 = 0.3561 * 100 = 35.61(\%)$$

$$C_{NDC}: NDC - VEH = 188.20(\%) - 100(\%) = 88.20(\%) = 0.8820$$

$$\text{Bliss value} = C_{NDC} - C_{Bliss} = 0.8820 - 0.3561 = 0.5259$$

Bliss value of NDC (0.5259) is greater than zero indicating that the two drugs in the NDC are synergistic in improving motor coordination.

Mean values from graph shown in FIG. 15 on day 7: VEH (33.78), DONE (30.61), NAC (38.01), NDC (49.36)

$$C_{Done}: \text{DONE} - VEH = 90.61(\%) - 100(\%) = -9.39(\%) = -0.0939$$

$$C_{NAC}: NAC - VEH = 112.51(\%) - 100(\%) = 12.51(\%) = 0.1251$$

$$C_{Bliss} = C_{Done} + C_{NAC} - C_{Done} * C_{NAC} = -0.0939 + 0.1251 - ((-0.0939) * (0.1251)) = 0.0430$$

$$\text{Predicted response} = C_{Bliss} * 100 = 0.0430 * 100 = 4.30(\%)$$

$$C_{NDC}: NDC - VEH = 146.12(\%) - 100(\%) = 46.12(\%) = 0.4612$$

$$\text{Bliss value} = C_{NDC} - C_{Bliss} = 0.4612 - 0.0430 = 0.4182$$

Bliss value of NDC (0.4182) is greater than zero indicating that the two drugs in the NDC are synergistic in improving motor coordination.

Mean values from FIG. 15 on day 14: VEH (48.47), DONE (39.30), NAC (40.65), NDC (79.41)
Normalized to VEH: VEH (100%), DONE (81.08%), NAC (83.86%), NDC (163.82%)

$$C_{Done}: \text{DONE} - VEH = 81.08(\%) - 100(\%) = -18.92(\%) = -0.1892$$

$$C_{NAC}: NAC - VEH = 83.86(\%) - 100(\%) = -16.14(\%) = -0.1614$$

$$C_{Bliss} = C_{Done} + C_{NAC} - C_{Done} * C_{NAC} = -0.1892 + (-0.1614) - ((-0.1892) * (-0.1614)) = -0.3811$$

$$\text{Predicted response} = C_{Bliss} * 100 = (-0.3811) * 100 = -38.11(\%)$$

$$C_{NDC}: NDC - VEH = 163.82(\%) - 100(\%) = 63.82(\%) = 0.6382$$

$$\text{Bliss value} = C_{NDC} - C_{Bliss} = 0.6382 - (-0.3811) = 1.0193$$

Bliss value of NDC (1.0193) is greater than zero indicating that the two drugs in the NDC are synergistic in improving motor coordination.

Mean values from FIG. 15 on day 21: VEH (63.76), DONE (49.53), NAC (28.67), NDC (102.38)

Normalized to VEH: VEH (100%), DONE (77.68%), NAC (44.96%), NDC (160.55%)

$$C_{Done}\text{: DONE} - VEH = 77.68(\%) - 100(\%) = -22.32(\%) = -0.2232$$

$$C_{NAC}\text{: } NAC - VEH = 44.96(\%) - 100(\%) = -55.04\ (\%) = -0.5504$$

$$C_{Bliss} = C_{Done} + C_{NAC} - C_{Done} * C_{NAC} = -0.2232 + (-0.5504) - ((-0.2232) * (-0.5504)) = -0.8964$$

$$\text{Predicted response} = C_{Bliss} * 100(-0.8964) * 100 = -89.64(\%)$$

$$C_{NDC}\text{: } NDC - VEH = 160.55(\%) - 100(\%) = 60.55(\%) = 0.6055$$

$$\text{Bliss value} = C_{NDC} - C_{Bliss} = 0.6055 - (-0.8964) = 1.5019$$

Bliss value of NDC (1.5019) is greater than zero indicating that the two drugs in the NDC are synergistic in improving motor coordination.

Improvement in Brain Damage—Immunohistochemical Assay

At 21 days after 45 minutes-MCAO-reperfusion modelling, brains were fixed in 4% paraformaldehyde in phosphate buffered saline (PBS) for 2 hours at 4° C., incubated with 30% sucrose at 4° C. for 16~24 hours. Brains were embedded in OCT compound and cryosections (30-μm thickness) were performed at 30 micro-meter of thickness. After washing with PBS, sections were incubated with blocking solution (4% normal goat serum in PBST) for 1 hour. For fluorescence immunohistochemistry (IHC), rabbit polyclonal GFAP antibody (AbFrontier, AR09-PA0002), mouse polyclonal NeuN (Millipore, MAB377) antibodies were applied to sections with a 1:200-500 dilution at 4° C. for 24 hours. After rinsing with PBST, sections were incubated with anti-rabbit Alexa 594 secondary antibody (Invitrogen, A-11012) or anti-mouse Alexa 488 secondary antibody (Invitrogen, A-10680) at a 1:500 dilution for 2 hours at room temperature. Sections were mounted with fluorescence mounting medium (Dako, 53023) and observed using a Lionheart LX Automated Microscope (BioTek). Infarcted region in the ipsilateral hemisphere was calculated by subtracting non-infarcted area from the contra lateral hemisphere. Then the value was divided by the contra lateral hemisphere and multiplied by 100. The assessment of infarct volume was done with image J software. Infarct vol. (%)=(contra lateral hemisphere area-non-infarcted area in ipsilateral hemisphere area)/contra lateral hemisphere area×100.

It is well known that MCAO results in injury to striatum, cortex and hippocampus region depending upon the time of occlusion of MCA and reperfusion period, leading to injured or infarcted brain region. As can be seen from FIG. 16, rats treated with the combination of donepezil HCl and NAC (NDC) show a significant reduction in the degree of brain damage (decrease in relative infarct volume) when compared with the vehicle group (no treatment is given). (*P<0.05, one-way ANOVA).

Activation of ERK and PI3K-AKT Pathways—Western Blot Assay

Figure 16:
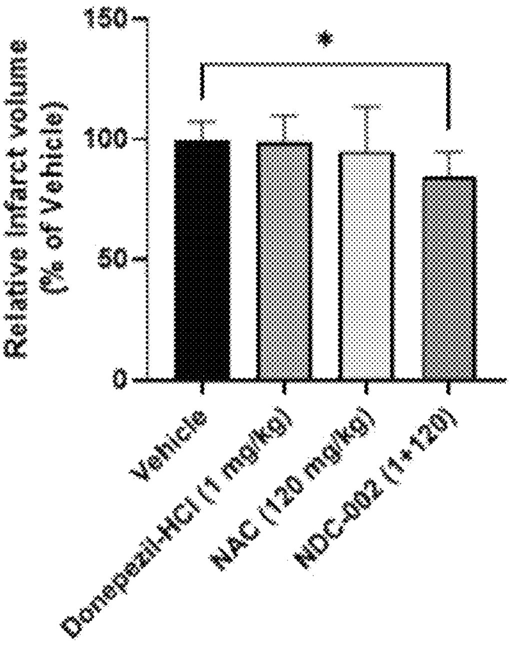
FIG. 16 illustrates the improvement in degree of brain damage (infarct volume) after treatment with donepezil alone, N-acetylcysteine alone, or a combination of donepezil and N-acetylcysteine using a stroke-reperfusion animal model.

As seen in FIG. 15 and FIG. 16, and as explained above, the testing done using in vivo models of stroke showed that the administration of combination of donepezil HCl and NAC to ischemic rats significantly and synergistically improved motor coordination and significantly reduced brain damage, compared to treatments with donepezil HCl alone, NAC alone or no treatment. The underlying mechanism of this neuroprotectant effect of NDC was further verified, and it was observed that donepezil HCl and NAC synergistically assert neuroprotection by activating the PI3K-AKT and ERK pathways.

At 21 days after 45-minutes-MCAO-reperfusion modeling, brains were collected to perform a western blot assay. Brains were homogenized in lysate buffer with protease inhibitor cocktail on ice. Each sample was centrifuged at 13,000 rpm and 4° C. for 30 minutes and the supernatant was used for further experiments. Protein concentration was measured using DC (Bio-rad, #5000112) protein assay. Samples were loaded using the SDS-PAGE system (Bio-rad, #1658004 and #1645052) and transferred onto nitrocellulose membranes (Bio-rad, #17001917 and #1704272). The membranes were blocked for 1 hour at room temperature with Tris-buffered saline-Tween20 (TBS-T) containing 5% skim milk and then incubated with pAKT antibody (Cell signaling, #4060), AKT primary antibody (Santacruz, SC-81434), EPO primary antibody (SCBT, SC-5290), ERK (CST, #9102), pERK (CST, #9101) and GAPDH (Bioworld, #MBOO1H) in 5% skim milk overnight at 4° C. Next day, the membranes were washed 3 times in TBS-T for 5 minutes, incubated with horseradish peroxidase-conjugated (HRP-conjugated) secondary antibody or fluorescence conjugated secondary antibody for 1-2 hours, and then washed 3 times in TBS-T for 5 minutes again. After final wash, the membranes were developed for chemiluminescence or fluorescence system. The signals of chemiluminescence or fluorescence were acquired and quantified by using ECL solution (Bio-rad, #1705062), iBright 1500 (Invitrogen, #CL1500), and Odyssey CLx (LI-COR, #CLX-2383) imaging system.

Figures 17A, 17B:
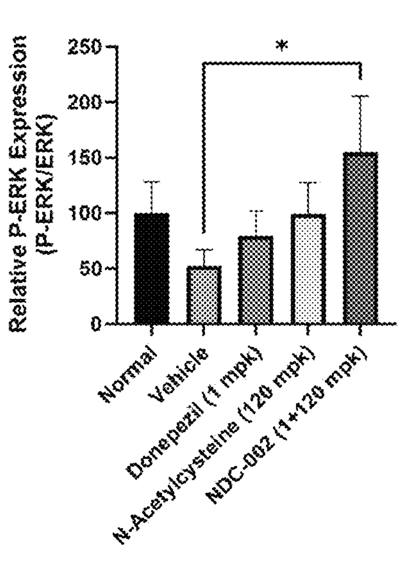
FIG. 17A illustrates the underlying mechanism of neuroprotectant effect of combination of donepezil and N-acetylcysteine via activation of PI3K-AKT pathway.
FIG. 17B illustrates the underlying mechanism of neuroprotectant effect of combination of donepezil and N-acetylcysteine via activation of ERK pathway.

The results of ex-vivo studies, presented in FIG. 17, show that 1 mpk donepezil HCl and 120 mpk NAC, when used alone, did not activate the PI3K-AKT and ERK pathways. However, as seen in FIG. 17A, surprisingly, the combination of 1 mpk donepezil HCl and 120 mpk NAC significantly increased the expression of pAKT, when compared to the vehicle (no treatment) or the treatment with 1 mpk donepezil HCl or 120 mpk NAC alone, indicating the activation of PI3K-AKT pathway. Further, as seen in FIG. 17B, the combination of 1 mpk donepezil HCl and 120 mpk NAC also significantly increased the expression of pERK when compared to the vehicle (no treatment), indicating the activation of ERK pathway. (*P<0.05, ***P<0.001 one-way ANOVA). Additionally, the below Bliss Independence calculations show that the combination of donepezil HCl and NAC exhibits a synergistic effect in activation of PI3K-AKT and ERK pathways. The actual effect of NDC ($C_{NDC}$) in increasing the expression of pAKT and pERK is greater than the predicted effect ($C_{Bliss}$) calculated using Bliss Independence model.

Mean values from graph in FIG. 17A: VEH (79.16), DONE (307.50), NAC (44.23), NDC (1029.83)

Normalized to VEH: VEH (100%), DONE (388.48%), NAC (55.88%), NDC (1301.02%)

$$C_{Done}\text{: DONE} - VEH = 388.48(\%) - 100(\%) = 288.48(\%) = 2.8848$$

$$C_{NAC}\text{: } NAC - VEH = 55.88(\%) - 100(\%) = -44.12(\%) = -0.4412$$

-continued $C_{Bliss}$ =

$$C_{Done}+C_{NAC}=2.8848+(-0.4412)-(2.8848*(-0.4412))=3.7164$$

$$\text{Predicted response}=C_{Bliss}*100=3.7164*100=371.64$$

$$C_{NDC}\text{: } NDC-VEH=1301.02(\%)-100(\%)=1201.02(\%)=12.0102$$

$$\text{Bliss value}=C_{NDC}-C_{Bliss}=12.0102-3.7164=8.2938$$

Bliss value of NDC (8.2938) is greater than zero, indicating that the two drugs in the NDC are synergistic in increasing the expression of pAKT, and, hence, the activation of PI3KT-AKT pathway.

Mean values from graph in FIG. 17B: VEH (52.43), DONE (79.67), NAC (99.50), NDC (154.66)
Normalized to VEH: VEH (100%), DONE (151.96%), NAC (189.77%), NDC (294.98%)

$$C_{Done}\text{: DONE}-VEH=151.96(\%)-100(\%)=51.96(\%)=0.5196$$

$$C_{NAC}\text{: } NAC-VEH=189.77(\%)-100(\%)=89.77(\%)=0.8977$$

$$C_{Bliss}=C_{Done}+C_{NAC}-C_{Done}*C_{NAC}=0.5196+(0.8977)=(0.5196*0.8977)=0.9509$$

$$\text{Predicted response}=C_{Bliss}*100=0.9509*100=95.09$$

$$C_{NDC}\text{: } NDC-VEH=294.98(\%)-100(\%)=194.98(\%)=1.9498$$

$$\text{Bliss value}=C_{NDC}-C_{Bliss}=1.9498-0.9509=0.9989$$

Bliss value of NDC (0.9989) is greater than zero, indicating that the two drugs in the NDC are synergistic in increasing the expression of pERK, and, hence, the activation of ERK pathway.

The combination of donepezil and NAC also caused an increased in erythropoietin (herein referred to as "EPO"), a known neuroprotectant which mediates the EPO receptor and downstream PI3K-AKT and ERK pathways. It is known that the therapeutic effect of EPO in improvement of brain damage occurs by simultaneous activation of PI3K-AKT and ERK pathways. The increase in EPO levels and activation of PI3K-AKT and ERK pathways due to synergistic effect of donepezil and NAC further illustrate their therapeutic use a neuroprotectant.

At 21 days after 45-minutes-MCAO (middle cerebral artery occlusion)-reperfusion modeling, brains were collected to perform the western blot assay. Brains were homogenized in lysate buffer with protease inhibitor cocktail on ice. Each sample was then centrifuged at 13,000 rpm and 4° C. for 30 minutes and the supernatant was used for further experiments. Protein concentration was measured using DC (Bio-rad, #5000112) protein assay. Samples were loaded using the SDS-PAGE system (Bio-rad, #1658004 and #1645052) and transferred onto nitrocellulose membranes (Bio-rad, #17001917 and #1704272). The membranes were blocked for 1 hour at room temperature with Tris-buffered saline-Tween20 (TBS-T) containing 5% skim milk and then incubated with pAKT antibody (Cell signaling, #4060), AKT primary antibody (Santacruz, SC-81434), EPO primary antibody (SCBT, SC-5290), ERK (CST, #9102), pERK (CST, #9101) and GAPDH (Bioworld, #MBOO1H) in 5% skim milk overnight at 4° C. Next day, the membranes were washed 3 times in TBS-T for 5 minutes, incubated with horseradish peroxidase-conjugated (HRP-conjugated) secondary antibody or fluorescence conjugated secondary antibody for 1-2 hours, and then washed 3 times in TBS-T for 5 minutes again. After final wash, the membranes were developed for chemiluminescence or fluorescence system. The signals of chemiluminescence or fluorescence were acquired and quantified by using ECL solution (Bio-rad, #1705062), iBright 1500 (Invitrogen, #CL1500), and Odyssey CLx (LI-COR, #CLX-2383) imaging system.

Figure 18:
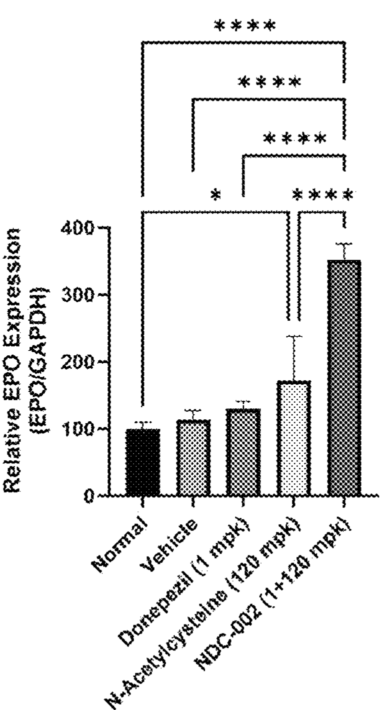
FIG. 18 illustrates the increase in EPO expression by the combination of donepezil and N-acetylcysteine further verifying the activation of PI3K-AKT and ERK pathways.

The results of ex-vivo studies, presented in FIG. 18, show that the EPO expression significantly increased upon treatment with combination of donepezil and NAC as compared to no treatment or treatment with donepezil alone or NAC alone. Additionally, the below Bliss Independence calculations show that the combination of donepezil HCl and NAC exhibits a synergistic effect in increasing the EPO expression. The actual effect of NDC ($C_{NDC}$) in increasing the EPO expression is greater than the predicted effect ($C_{Bliss}$) calculated using Bliss Independence model.

Mean values from graph in FIG. 18: VEH (113.69), DONE (130.04), NAC (172.43), NDC (352.72)
Normalized to VEH: VEH (100%), DONE (114.38%), NAC (151.66%), NDC (310.24%)

$$C_{Done}\text{: DONE}-VEH=114.38(\%)-100(\%)=14.38(\%)=0.1438$$

$$C_{NAC}\text{: } NAC-VEH=151.66(\%)-100(\%)=51.66(\%)=0.5166$$

$$C_{Bliss}=C_{Done}+C_{NAC}-C_{Done}*C_{NAC}=0.1438+0.5166-(0.1438*0.5166)=0.5861$$

$$\text{Predicted response}=C_{Bliss}*100=0.5861*100=58.61(\%)$$

$$C_{NDC}\text{: } NDC-VEH=310.24(\%)-100(\%)=210.24(\%)$$

$$\text{Bliss value}=C_{NDC}-C_{Bliss}=2.1024-0.5861=1.5163$$

Bliss value of NDC (1.5163) is greater than zero, indicating that the two drugs in the NDC are synergistic in increasing the expression of EPO, and, hence, causing neuroprotection.

INDUSTRIAL APPLICABILITY

The pharmaceutical composition of the present invention containing an antioxidant as an active ingredient exhibits an effect of preventing, alleviating, or treating one or more adverse effects that may occur due to the administration of a cholinesterase inhibitor in a therapeutically effective amount or more. Accordingly, the industrial applicability is very high as it not only mitigates the risk of adverse effects caused by the administration of the cholinesterase inhibitor in a therapeutically effective amount, but it can also be very useful for the treatment of subjects who require administration of the cholinesterase inhibitor in a therapeutically effective amount or more. Also, the composition comprising a cholinesterase inhibitor and an antioxidant, according to the present disclosure, exhibits enhanced preventive and therapeutic effects of brain diseases and/neurodegenerative disease as compared to their single administration, and have the effect of alleviating side effects that may be caused by excessive dosage or long-term administration of the cholinesterase inhibitor, therefore, there is high industrial availability.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating a brain disease, the method comprising administering donepezil and acetylcysteine or danthron to a subject in need thereof.

2. The method of claim 1, wherein the brain disease is selected from the group consisting of ischemic brain disease, Alzheimer's disease, and dementia.

3. A method of claim 2, wherein the ischemic brain disease is selected from the group consisting of stroke, cerebral hemorrhage, cerebral infarction, head trauma, cerebral circulatory metabolic disorder, vascular dementia, and cerebral functional coma.

4. The method as claimed in claim 1, wherein the method comprises administration of the acetylcysteine or danthron before, simultaneously with, or after administration of donepezil.

* * * * *